(12) United States Patent
Colman et al.

(10) Patent No.: US 6,969,357 B1
(45) Date of Patent: Nov. 29, 2005

(54) GAS ANALYZER CALIBRATION CHECKING DEVICE

(75) Inventors: Lewis Colman, Jerusalem (IL); Gershon Levitsky, Jerusalem (IL); Ilan Ben-Oren, Jerusalem (IL)

(73) Assignee: Oridion Breathid Ltd., Jerusalem (IL)

( * ) Notice: Subject to any disclaimer, the term of this patent is extended or adjusted under 35 U.S.C. 154(b) by 76 days.

(21) Appl. No.: 10/009,846

(22) PCT Filed: Jun. 7, 2000

(86) PCT No.: PCT/IL00/00338

§ 371 (c)(1),
(2), (4) Date: Mar. 29, 2002

(87) PCT Pub. No.: WO00/74553

PCT Pub. Date: Dec. 14, 2000

Related U.S. Application Data

(63) Continuation of application No. 09/542,768, filed on Apr. 4, 2000, now Pat. No. 6,656,127.

(30) Foreign Application Priority Data

Jun. 8, 1999 (IL) ...................................... 130370

(51) Int. Cl.$^7$ ............................ A61B 5/08; G01N 1/22
(52) U.S. Cl. ...................... 600/529; 600/532; 73/23.3; 422/84
(58) Field of Search ..................... 600/529, 531–533, 600/538, 543; 73/23.3; 128/920, 923–925; 422/84, 83

(56) References Cited

U.S. PATENT DOCUMENTS 3,830,630 A  8/1974 Kiefer
4,390,483 A  6/1983 Willems et al.
4,448,058 A  5/1984 Jaffe et al.
4,490,482 A  12/1984 Mathieu
4,639,432 A  1/1987 Holt et al.
4,680,956 A  7/1987 Huszczuk
4,684,805 A  8/1987 Lee et al.
4,723,435 A  2/1988 Huszczuk (Continued)

FOREIGN PATENT DOCUMENTS

DE  19714903  10/1998

(Continued)

OTHER PUBLICATIONS

Israeli, E. et al., "Continuous, Real Time Measurement with a Novel 13C-Breath Analyzer: Faster Urea Breath Test Results with High Accuracy", Gastrenterology, vol. 116(4), Apr. 1999, p. a-195.

(Continued)

*Primary Examiner*—Max F. Hindenburg
*Assistant Examiner*—Navin Natnithithadha
(74) *Attorney, Agent, or Firm*—Darby & Darby

(57) ABSTRACT

A calibration checking device, and methods of mandating its use at regular time intervals, to ensure maintenance of the accuracy of gas analyzers, especially for use with breath tests, Each calibration checking device is designed to be used for a predetermined number of tests. After first connection of a new calibration checking device, a volume of known calibration checking gas is released into the instrument, and a calibration checking measurement is initiated. A signal is sent to a counting mechanism which both enables the use of the instrument, and commences a count of the number of tests performed by the breath tester. When the number of tests is exceeded, the instrument is disenabled. The device can include a moisture filter having an interface with the instrument, which prevents its operation if the filter is used beyond the recommended number of times, or if excess moisture renders it saturated.

26 Claims, 18 Drawing Sheets

U.S. PATENT DOCUMENTS

| | | | |
|---|---|---|---|
| 4,732,435 A | | 3/1988 | Huszczuk |
| 4,756,000 A | | 7/1988 | Macken |
| 4,757,512 A | | 7/1988 | Macken |
| 4,926,164 A | * | 5/1990 | Porter et al. ................. 340/576 |
| RE33,493 E | | 12/1990 | Lee et al. |
| 5,127,406 A | | 7/1992 | Yamaguchi |
| 5,146,294 A | | 9/1992 | Grisar et al. |
| 5,239,492 A | * | 8/1993 | Hartwig et al. ............... 702/27 |
| 5,300,859 A | | 4/1994 | Yatsiv et al. |
| 5,303,575 A | * | 4/1994 | Brown et al. ................. 73/23.3 |
| 5,317,156 A | * | 5/1994 | Cooper et al. ............... 250/345 |
| 5,357,971 A | * | 10/1994 | Sheehan et al. ............ 600/532 |
| 5,394,236 A | * | 2/1995 | Murnick ...................... 356/311 |
| 5,479,019 A | * | 12/1995 | Gross ......................... 250/345 |
| 5,486,699 A | | 1/1996 | Fabinski et al. |
| 5,543,621 A | | 8/1996 | Sauke et al. |
| 5,640,014 A | | 6/1997 | Sauke et al. |
| 5,657,750 A | | 8/1997 | Colman et al. |
| 5,747,809 A | | 5/1998 | Eckstrom |
| 5,752,504 A | * | 5/1998 | Bathe ..................... 128/203.12 |
| 5,818,580 A | | 10/1998 | Murnick |
| 5,908,789 A | * | 6/1999 | Weckstrom ................... 422/84 |
| 5,944,670 A | | 8/1999 | Katzman |
| 5,957,858 A | * | 9/1999 | Micheels et al. ........... 600/532 |
| 5,962,335 A | | 10/1999 | Katzman |
| 5,964,712 A | * | 10/1999 | Kubo et al. ................. 600/532 |
| 6,067,989 A | | 5/2000 | Katzman |
| 6,096,558 A | | 8/2000 | Stock |
| 6,106,479 A | | 8/2000 | Wunderlich et al. |
| 6,234,001 B1 | * | 5/2001 | Sorensen et al. ............ 73/1.04 |
| 6,656,127 B1 | * | 12/2003 | Ben-Oren et al. .......... 600/532 |

FOREIGN PATENT DOCUMENTS

| | | |
|---|---|---|
| DE | 19735599 | 3/1999 |
| EP | 0 253 927 | 1/1988 |
| EP | 0 415 600 | 3/1991 |
| EP | 0 860 170 | 3/2000 |
| GB | 1 591 709 | 6/1981 |
| GB | 2 324 387 A1 | 10/1998 |
| WO | WO 96/14091 | 5/1996 |
| WO | WO 98/21579 | 5/1998 |
| WO | WO 98/30888 | 7/1998 |
| WO | WO 99/12471 | 3/1999 |
| WO | WO 99/14576 | 3/1999 |

OTHER PUBLICATIONS

NASA, "Low-Temperature Oxidation Catalysts", Oct. 1995, pp. 1-2, http://tag-www.larc.nasa.gov/tops.

Schoeller, et al., "13C Abundances of Nutrients and the Effect of Variatins in 13c Isotopic Abundances of Test Meals Formulated for 13CO2 Breath Test1-3", American Journal of Clinical Nutrition, Chap. 33, Nov. 1980, pp. 2375-2385.

"The ABC-NT Gas Isotope Ratio Mass Spectrometer", 510(k) Summary, K974322, Nov. 1997, pp. 1-9.

Kalach, et al. "The 13Carbon Urea Breath Test for the Noninvasive Detection of *Helicobacter pylori* in Children: Comparison with Culture and Determination of Minimum Analysis Requirements", Journal of Pediatric Gastroenterology and Nutrition, vol. 26, Mar. 1998, pp. 291-296.

STC Catalysts, Inc., "Catalysts for Long-life CO2 Lasers", Nov. 1996, pp. 1-4, http://www.stcnet.com.

U.S. Appl. No. 08/961,013, filed Oct. 30, 1997, entitled: "Fluid Analyzer With Tube Connector Verified".

Graham, D. Y. et al., "Citric Acid as the Test Meal for the 13C-Urea Breath Test", American Journal of Gastroenterology, vol. 94, May 1999, pp. 1214-1217.

Alimetrics, "Pylori-Check Breath test kit", 08-0190 Rev 0C, USA, 1999, pp. 1-18.

Oridion Medical Ltd., "BreathID Profile", pp. 1-8, Feb. 1999, Israel.

Haisch, "Quantitative Isotope-Selective Infra-Red Spectroscopy for Determining the Isotopic Ratio of Carbon Dioxide in Breath", Haisch Inaugural Dissertation, Heinrich Heine Universitaet, Duesseldorf, 1995, pp. 1-10. (A translation).

* cited by examiner

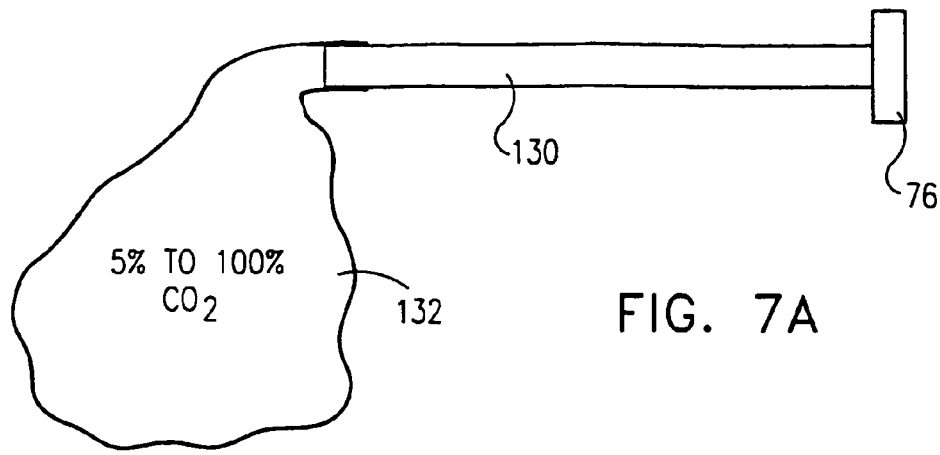
FIG. 7A
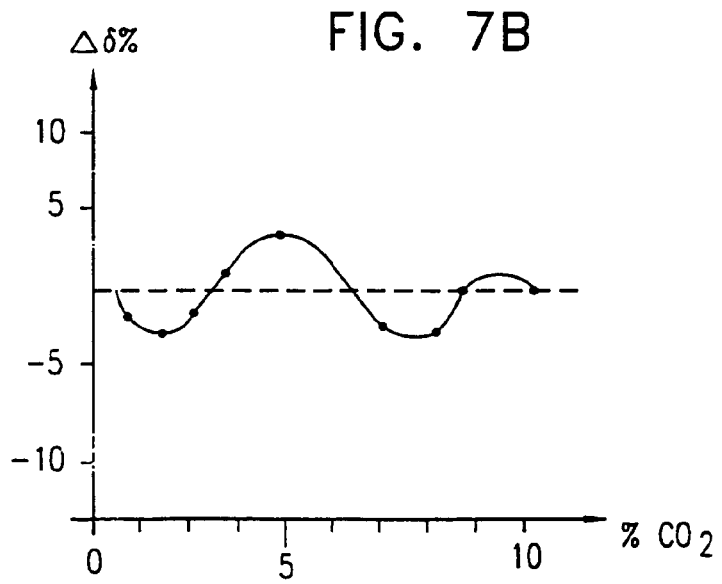
FIG. 7B
FIG. 8
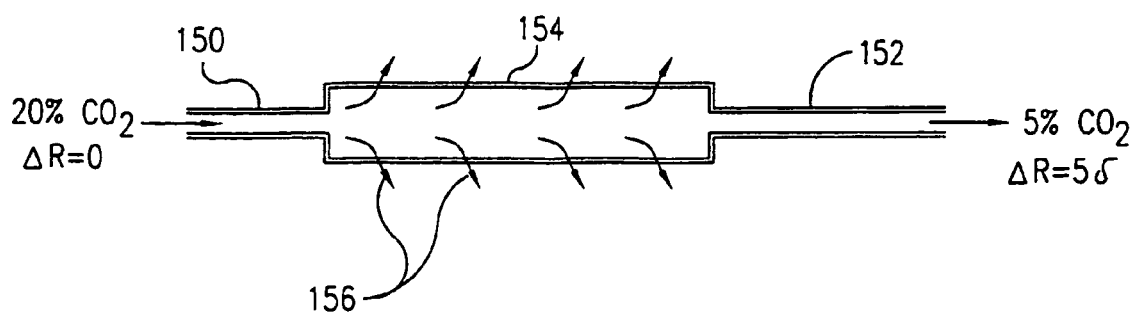

$$\Delta(^{12}CO_2) = (^{12}CO_2)_{in} - (^{12}CO_2)_{out}$$

$(^{12}CO_2)_{out} = 5\% = $ constant $Q = 250 ml/min = $ constant

GAS ANALYZER CALIBRATION CHECKING DEVICE

CROSS REFERENCE TO RELATED APPLICATIONS

This is the U.S. national phase application based upon international application no. PCT/IL00/00338 filed Jun. 7, 2000, published in English on Dec. 14, 2000, which is a continuation in part of U.S. application Ser. No. 09/542,768 filed Apr. 4, 2000 now U.S. Pat. No. 6,656,127. The entire disclosures of the prior applications are incorporated herein by reference.

FIELD OF THE INVENTION

The present invention relates to the field of gas analyzer calibration and filtering devices, especially for use with breath test instrumentation.

BACKGROUND OF THE INVENTION

Gas analyzers are used for many measurement and monitoring functions in science, industry and medicine. In particular, gas spectrometry is becoming widely used in diagnostic instrumentation based on the use of breath tests for detecting a number of medical conditions present in patients. Descriptions of much breath test methodology and instrumentation are disclosed in PCT Publication No. WO99/12471, entitled "Breath Test Analyzer" by D. Katzman and E. Carlebach. Methods of constructing and operating gas analyzers such as are used in breath test instrumentation are disclosed in PCT Publication No. WO99/14576, entitled "Isotopic Gas Analyzer" by I. Ben-Oren, L. Colman, E. Carlebach, B. Giron and G. Levitsky, some of whom are inventors in the present application. Each of the above documents is hereby incorporated by reference in its entirety.

Such breath tests are based on the ingestion of a marker substrate, which is cleaved by the specific bacteria or enzymic action being sought, or as a result of the metabolic function being tested, to produce marked by-products. These by-products are absorbed in the blood stream, and are exhaled in the patient's breath, where they are detected by means of the gas analyzer.

One well known method of marking such substrates is by substituting one of its component atoms with an isotopically enriched atom. Such substrates and their by-products are commonly called isotopically labeled. One atom commonly used in such test procedures is the non-radioactive carbon-13 atom, present in a ratio of about 1.1% of naturally occurring carbon. Using $^{13}C$ as the tracer, the cleavage product produced in many such tests is $^{13}CO_2$, which is absorbed in the bloodstream and exhaled in the patient's breath. The breath sample is analyzed, before and after taking this marker substrate, typically in a mass spectrometer or a non-dispersive infra-red spectrometer. Detected changes in the ratio of $^{13}CO_2$ to $^{12}CO_2$ may be used to provide information about the presence of the specific bacteria or enzymic action being sought, or as a measure of the metabolic function being tested.

Since the amount of $CO_2$ arising from the process under test may be a very small proportion of the total $CO_2$ production from all of the bodies' metabolic processes, the breath test instrumentation must be capable of detecting very small changes in the naturally occurring percentage of $^{13}CO_2$ in the patient's breath. Typically, the instrument should be capable of detecting changes of a few parts per million in the level of $^{13}CO_2$ in the patient's exhaled breath, where the whole $^{13}CO_2$ content in the patient's exhaled breath is only of the order of a few hundred ppm. For this reason, the sensitivity, selectivity and stability of the gas analyzers used in such tests must be of the highest possible level to enable accurate and speedy results to be obtained.

In order to maintain the reliability of such tests, it is necessary to ensure that the calibration of the gas analyzer is maintained at the correct level. For this reason, in order to ensure maintenance of the high accuracy levels required, many of the prior art instruments necessitate the performance of complex and time-consuming calibration procedures, some of which have to be laboratory performed, rather than user-performed in the field. Since the advent of compact and low cost breath test instrumentation is making breath testing a widely used medical office procedure, instead of a hospital or laboratory procedure, the need for simple, user-performed, periodic calibration checks is becoming of prime importance.

Furthermore, the breath exhaled by patients always contains a naturally high level of humidity, and in the case of intubated patients, could also contain a high level of moisture and other secretions. The presence of such extraneous fluids can severely affect the ability of the gas analyzer to accurately measure the sought-after gas. Furthermore, constant exposure to high levels of humidity can have an adverse effect on the component parts of the gas analyzer, and especially on the measuring sensor itself. For these reasons, moisture and humidity filters are advisable to maintain the accuracy of the instrument. Since the operator may have a tendency to use the filters provided with the instrument beyond the recommended number of times, thereby impairing the accuracy of the measurement, it is important that means be adopted to ensure that the filtration unit is not used beyond its stated lifetime.

There therefore exists a need to ensure the maintenance of the accuracy of breath test instrumentation, both by means of regularly mandated calibration checks, and by ensuring regular mandated changes of the moisture filter used with the instrument. Furthermore, there is a need for the calibration checking procedure to be capable of simple and preferably semi-automatic execution by the user, rather than requiring the intervention of a technician, or shipment to a calibration laboratory.

The disclosures of all publications mentioned in this section and in the other sections of the specification, are hereby incorporated by reference, each in its entirety.

SUMMARY OF THE INVENTION

The present invention seeks to provide new methods and devices for ensuring the accuracy and reliability of breath tests, by the use of system and calibration checking devices, optionally incorporating filtering devices, and methods of ensuring their periodic use.

The term "system check" is often used, to describe methods for determining that multiple aspects of the measurement system are functioning correctly, including primarily calibration of the gas analyzer, but also possibly including such functions as the radiation source stability, the input capnograph calibration, the gas handling system, the intermediate chamber system for collecting and diluting accumulated breath samples, and the detector operation.

The term "calibration check" is generally used in this specification and claimed, to refer to a measurement of the absolute calibration of the isotopic ratios measured by the breath tester, referred to a zero base line level. Such a calibration check is executed by the use of calibration checking gases with known isotopic concentrations or ratios, input to the instrument from externally supplied containers. Since a calibration check is part of a system check, overlapping use of the terms may have been made on occasion, according to the context under discussion.

The present invention first of all seeks to provide a new system checking device for use with gas analyzer-based breath test instrumentation, including the ability to perform a calibration check of the instrument against known calibrating gases. The use of the device with breath tests is particularly important, because of the high sensitivity, selectivity and accuracy, which must be maintained to ensure the success of such tests. The use of the device is simple, and ensures that the overall functionality and accuracy of the gas analyzer is checked at regular predetermined periods, without the need for the operator to perform complex calibration procedures. At the same time, the calibration checking device may also comprise a fluid filter, and is so constructed that its use ensures efficient fluid filtering.

There is thus provided in accordance with a preferred embodiment of the present invention, a calibration checking sampling line unit with a built-in filter, particularly for use with breath test instrumentation. In order to maintain the guaranteed accuracy of the breath test, it is important both to perform regular calibration checks of the gas monitor, and to ensure that the humidity level of the sampled gas is kept below a specified level, and that there is no liquid penetration into the gas analyzer. Each calibration checking device is designed to be used for a predetermined number of tests, preferably with a separate disposable oral/nasal part for each individual test performed, as is usual clinical practice. After first connection of a new calibration checking device, according to one preferred embodiment of the present invention, a volume of known calibration checking gas is released into the instrument, and calibration checking measurement is initiated. At the same time, a signal is sent to a counting mechanism which both enables the use of the instrument, and commences a count of the number of tests performed by the breath tester. The counting mechanism can be located either on the calibration checking device or in the instrument itself. When the predetermined number of tests have been performed, after which a new calibration check is recommended, the counting mechanism provides operator warning thereof, or preferably even prevents continued operation of the instrument until a new calibration check is performed. A preferred method for performing this control function is disclosed in a further embodiment of the present invention.

According to another preferred embodiment of the present invention, the signal transmitted after first connection of a new calibration checking device and performance of a calibration checking procedure, is sent to a timing mechanism which both enables the use of the instrument, and begins accumulating the amount of time that the breath tester has been in operation since the last calibration checking procedure. When a predetermined operation time has been exceeded, after which a new calibration check is recommended, the timer mechanism provides operator warning thereof, or preferably even prevents continued operation of the instrument until a new calibration check is performed.

According to a further preferred embodiment of the present invention, the built-in moisture filter also has an interface with the instrument, which prevents its operation if the filter is used beyond the recommended number of times, or if excess moisture renders it saturated. As an alternative to a multiple-use filter unit, the disposable oral/nasal part supplied for each individual test is provided with a built-in section of moisture filtering or moisture absorbing material, to ensure the use a fresh filter element for every patient test. According to this embodiment of the invention, the use of a fresh filter, while not mandated, should be performed automatically if normal hygienic clinical procedures of using a new cannula for every test are followed. In this case, to give additional assurance that a new cannula would be used for every test, each calibration check unit is preferably supplied as a kit with the number of disposable oral/nasal parts, which would suffice for the number of tests expected to be performed within the recommended changing period of the calibration check unit.

In accordance with further preferred embodiments of the present invention, where the particular circumstances of the test conditions allow it, the calibration checking device can incorporate a calibration check unit only, without a filter device, or a filter device only, without any calibration check unit. Alternatively and preferably, the calibration checking device can contain both a calibration check unit and a filter unit, and the enable or count signal transmitted to the instrument from only one or other of the two units. Alternatively and preferably, the enable signal is transmitted to the instrument from both of the two units, and the system enabled only when both provide the necessary authorization signal.

According to further preferred embodiments of the present invention, the calibration checking device is used in co-operation with a breath simulating device inside the breath tester, the combination operating as a complete system checking device. From the calibration checking device gas fill, a series of gas samples is produced which simulate all aspects of the breath of a subject undergoing a breath test. According to these embodiments, the breath simulator provides samples of (i) ambient air with the natural level of the breath test gas, to simulate the inhaled breath, (ii) a sample of the gas to be detected in the breath test with a known low isotopic ratio, to simulate the exhaled breath of a subject before ingestion of the isotopically labeled substrate, and (iii) a sample of the breath test gas having an isotopic ratio of the detected component somewhat increased, to simulate the exhaled breath of a subject having a detectable response to the breath test. The supply of these three types of calibration check input gases, and the timing of their supply, is preferentially provided by means of a pneumatic system using solenoid valves to route the gases through the correct paths, and at the correct timing rate to simulate human respiration rate. According to alternative preferred embodiments, the calibration checking gas with the slightly raised isotopic ratio component is generated either by means of a porous tube device, able to preferentially change the isotopic content of a gas flowing through it, or by means of two separate calibration checking gas containers, each containing a gas fill with a slightly different isotopic ratio.

In accordance with yet other preferred embodiments of the present invention, there is provided a breath simulator device for checking the system functionality of a breath test instrument, which provides gas samples to simulate exhaled breaths of a subject. This simulation of exhaled breaths can be any one or more of the properties including flow rate, total gas species concentration, isotopic ratio of the gas species sample, and respiration rate.

There is further provided in accordance with yet another preferred embodiment of the present invention, a calibration checking device consisting of a porous tube which allows preferential diffusion through its wall of one component of a calibrating gas. The porous tube can be such as to amend the isotopic ratio of a calibrating gas during passage through it.

In accordance with still another preferred embodiment of the present invention, there is provided a calibration checking device as described above and also consisting of gas switching means for alternating the output of the device between calibration gas with and without an amended isotopic ratio. Furthermore, the gas switching means can also be operative for alternating the output of the device between calibration gas with an amended isotopic ratio, calibration gas without an amended isotopic ratio, and air without any calibrating gas. The gas switching means operates, according to a further preferred embodiment, at a switching rate in a range similar to human respiration rate.

There is further provided in accordance with still another preferred embodiment of the present invention, a calibration checking device consisting of a calibrating gas inlet conduit supplying calibrating gas to a porous tube, the porous tube allowing preferential diffusion through its wall of one component of the calibrating gas, a calibrating gas outlet conduit, conveying calibrating gas with an amended composition from the porous tube, and an outer chamber through which the porous tube passes, the outer chamber being continually flushed with a purging gas to remove any component of the calibrating gas which diffuses through the wall of the porous tube.

In accordance with further preferred embodiments of the present invention, the calibration checking device as described above is also operative to amend the isotopic ratio of a calibrating gas during passage through it. Furthermore, it may also consist of gas switching means for alternating the output of the device between calibration gas with and without an amended isotopic ratio, or for alternating the output of the device between calibration gas with an amended isotopic ratio, calibration gas without an amended isotopic ratio, and air without any calibrating gas. In accordance with yet a further preferred embodiment of the present invention, the gas switching means operates at a switching rate in a range similar to a human respiration rate.

There is even further provided in accordance with another preferred embodiment of the present invention, a breath tester incorporating a calibration checking device as described above, and also including a receiver into which is inserted a container of calibrating gas, the receiver including means for enabling a calibration checking procedure in the breath tester. The container of calibrating gas can be made of glass, and insertion of the container into the receiver then actuates breakage of the glass, thereby releasing the calibrating gas. Furthermore, in accordance with yet another preferred embodiment of the present invention, the container of calibrating gas is closed by means of a pressure seated check valve, and insertion of the container into the receiver depresses the check valve, thereby releasing the calibrating gas.

In accordance with a further preferred embodiment of the present invention, the container of calibrating gas is closed by means of a thin metallic foil, and insertion of the container into the receiver enables a needle to penetrate the thin foil, thereby releasing the calibrating gas. Alternatively, the container of calibrating gas may be a hermetically sealed flexible plastic bag.

In accordance with yet another preferred embodiment of the present invention, there is provided a breath tester incorporating a calibration checking procedure, operative to ensure that the breath tester is enabled only if a routine mandatory calibration check is performed after a predetermined number of breath tests. In accordance with yet another preferred embodiment of the present invention, the calibration checking procedure is also operative to ensure that the breath tester is enabled only if an authorized and new container of calibration gas is used for the routine mandatory calibration check.

In accordance with still another preferred embodiment of the present invention, there is provided a method of calibrating a breath tester, consisting of the steps of performing a calibration check on the breath tester by the use of at least two gases having known isotopic ratio differences between them, comparing the deviation in the differences in the isotopic ratios measured by the breath tester from those of the at least two gases, and performing a calibration of the breath tester if the deviation exceeds a predetermined value.

There is further provided in accordance with still another preferred embodiment of the present invention, a calibration checking device for use with a gas analyzer, consisting of a calibration checking unit, and an enabling mechanism for enabling operation of the gas analyzer. In accordance with further preferred embodiments of the present invention, the enabling mechanism is operative to count the number of tests performed by the gas analyzer, or to accumulate the time of operation of the gas analyzer. In accordance with another preferred embodiment of the present invention, the enabling mechanism is actuated by the use of the calibration checking unit.

There is further provided in accordance with yet a further preferred embodiment of the present invention, a calibration checking-device for use with a gas as described above and also consisting of a filter for removing fluids from a gas to be analyzed. Furthermore, in accordance with yet another preferred embodiment of the present invention, the enabling mechanism for enabling operation of the gas analyzer operated by the filter.

There is also provided in accordance with a further preferred embodiment of the present invention, a calibration checking device for use with a gas as described above and wherein the enabling mechanism is communicative with the gas analyzer by means of an electrical, electronic, optical, mechanical, magnetic, pneumatic or gaseous signal.

In accordance with yet another preferred embodiment of the present invention, the enabling mechanism mentioned above is also operative to ensure proper location of the calibration checking unit.

There is further provided in accordance with yet another preferred embodiment of the present invention, a calibration checking device for use with a gas as described above and wherein the enabling mechanism consists of optical transmitter and receiver means, the optical path between which is completed by reflection from the calibration checking unit only when the calibration checking unit is properly located in the gas analyzer.

In accordance with still another preferred embodiment of the present invention, there is provided a calibration checking device for use with a gas analyzer, consisting of a calibration checking unit, and a count actuating mechanism initiated by first use of the calibration checking device, operative to begin a count of the number of tests performed with the calibration checking device. The calibration checking device described above can also include a filter for removing fluids from the gas to be analyzed.

There is further provided in accordance with still another preferred embodiment of the present invention, a calibration checking device for use with a gas analyzer as described above and wherein the count actuating mechanism is actuated by the calibration checking unit, or by the filter.

In accordance with a further preferred embodiment of the present invention, there is also provided a calibration checking device for use with a gas analyzer as described above and wherein the count is used to prevent use of the gas analyzer after a predetermined number of tests have been performed. The count of the number of tests performed with the calibration checking device may be performed within the gas analyzer, or within the calibration checking device.

There is provided in accordance with yet a further preferred embodiment of the present invention, a calibration checking device for use with a gas analyzer as described above and wherein the count actuating mechanism is communicative with the gas analyzer by means of an electrical, electronic, optical, mechanical, magnetic, pneumatic or gaseous signal.

There is provided in accordance with yet a further preferred embodiment of the present invention, a calibration checking device for use with a gas analyzer as described above and wherein the calibration checking unit releases a calibration checking gas of known composition into the gas analyzer. The enabling mechanism may be actuated by release of the calibration checking gas.

Furthermore, in accordance with yet another preferred embodiment of the present invention, there is provided a calibration checking device for use with a gas analyzer as described above and wherein the enabling mechanism is actuated by means of an active integrated circuit disposed on the calibration checking device.

There is also provided in accordance with a further preferred embodiment of the present invention, a calibration checking device for use with a gas analyzer as described above and wherein the count actuating mechanism is actuated by means of an active integrated circuit disposed on the calibration checking device. In accordance with yet other preferred embodiments of the present invention, the gas analyzers as described above, may also include a disenabling device which prevents the count actuating mechanism from being reinitiated after first use of the calibration checking device.

There is further provided in accordance with yet another preferred embodiment of the present invention, a calibration checking device for use with a gas analyzer as described above and wherein the filter is a section of a sampling tube having built-in fluid filtering properties. The filter may be operative for removing fluids from a gas to be analyzed, and may consist of a drying agent disposed in proximity to at least part of an inside wall of the sampling tube.

In accordance with still another preferred embodiment of the present invention, there is provided a calibration checking device for use with a gas analyzer as described above, and wherein the construction of the calibration checking unit and the filter are such as to essentially maintain the waveform of a breath of gas to be analyzed.

There is further provided in accordance with still another preferred embodiment of the present invention, a calibration checking device for use with a gas analyzer, consisting of a sampling line for conveying a gas to be analyzed to the gas analyzer, at least one enclosure housing at least one container of calibration gas, at least one mechanism for releasing the calibration gas in the at least one container into the enclosure, the mechanism having interactive control contact with the gas analyzer, and at least one delivery conduit connecting between the enclosure and the sampling tube for conveying the calibration gas after release into the sampling line. The interactive control contact may be the actuation of the mechanism by means of the gas analyzer. Alternatively, the interactive control contact may be the transmission of a signal to the gas analyzer on actuation of the mechanism.

In accordance with a further preferred embodiment of the present invention, there is also provided a calibration checking device for use with a gas analyzer as described above, and wherein the at least one container of calibration gas consists of two containers of calibration gas.

There is provided in accordance with yet a further preferred embodiment of the present invention, a calibration checking device for use with a gas analyzer as described above, and wherein the at least one delivery conduit consists of two delivery conduits.

There is even further provided in accordance with a preferred embodiment of the present invention, a calibration checking unit for use with a gas analyzer, consisting of a calibration gas mixture consisting of at least a first and a second gas, and a delivery conduit for conveying the calibration gas mixture to the gas analyzer, the delivery conduit consisting of a material which allows preferential diffusion through its wall of at least one of the at least a first and a second gas. Furthermore, in accordance with other preferred embodiments of the present invention, the material may be a selective membrane, or a porous diffusive tube.

There is also provided in accordance with a further preferred embodiment of the present invention, a kit for calibration checking a gas analyzer consisting of at least one calibration checking unit and a plurality of disposable sampling tubes for each of at least one calibration checking unit. In accordance with a further preferred embodiment, at least one of the sampling tubes may include a fluid filter.

In accordance with yet another preferred embodiment of the present invention, there is provided a kit for calibration checking a gas analyzer consisting of at least one calibration checking unit capable of interactive communication with the gas analyzer, and a plurality of disposable sampling tubes for each of the at least one calibration checking unit. In accordance with a further preferred embodiment, at least one of the sampling tubes may include a fluid filter.

There is further provided in accordance with yet another preferred embodiment of the present invention, a calibration checking unit operative to generate a second calibration material from a first material input thereto. The first material may also be a calibrating material. In accordance with still another preferred embodiment of the present invention, the materials may be gases for use in a gas analyzer.

There is further provided in accordance with still another preferred embodiment of the present invention, a breath bringer which changes a characteristic during use. The characteristic may be a color.

In accordance with a final preferred embodiment of the present invention, there is also provided a calibration checking device for use with a gas analyzer as described above and wherein the enabling mechanism is operative to accumulate the time since the last calibration check of the gas analyzer.

BRIEF DESCRIPTION OF THE DRAWINGS

The present invention will be understood and appreciated more fully from the following detailed description, taken in conjunction with the drawings in which:

FIG. 2A shows a connector incorporating a simple electrical contact interface and FIG. 2B shows a connector with an optical interface.

FIGS. 7A and 7B illustrate schematically the operational concepts which are the basis of the calibration checking methods according to preferred embodiments of the present invention. FIG. 7A shows a representation of a source of a calibrating gas of known concentrations, which can come from a variety of sources, while FIG. 7B shows a schematic graph of results typically obtained from a series of dilutions of the calibrating gas, and measurements of the isotopic ratio at each dilution;

FIG. 8 schematically shows a preferred embodiment of a porous tube for generating a gas sample with a different isotopic ratio to that input to the tube;

FIG. 16A shows the closed container, while FIG. 16B shows the calibration checking gas released by the act of screwing the container into the front panel connector of the breath tester. FIG. 16C shows a device for ensuring that the gas container is correctly located in the front panel input connector, when use is made of an alternative embodiment whereby the container is inserted by means of linear motion;

DETAILED DESCRIPTION OF PREFERRED EMBODIMENTS

Figure 1:
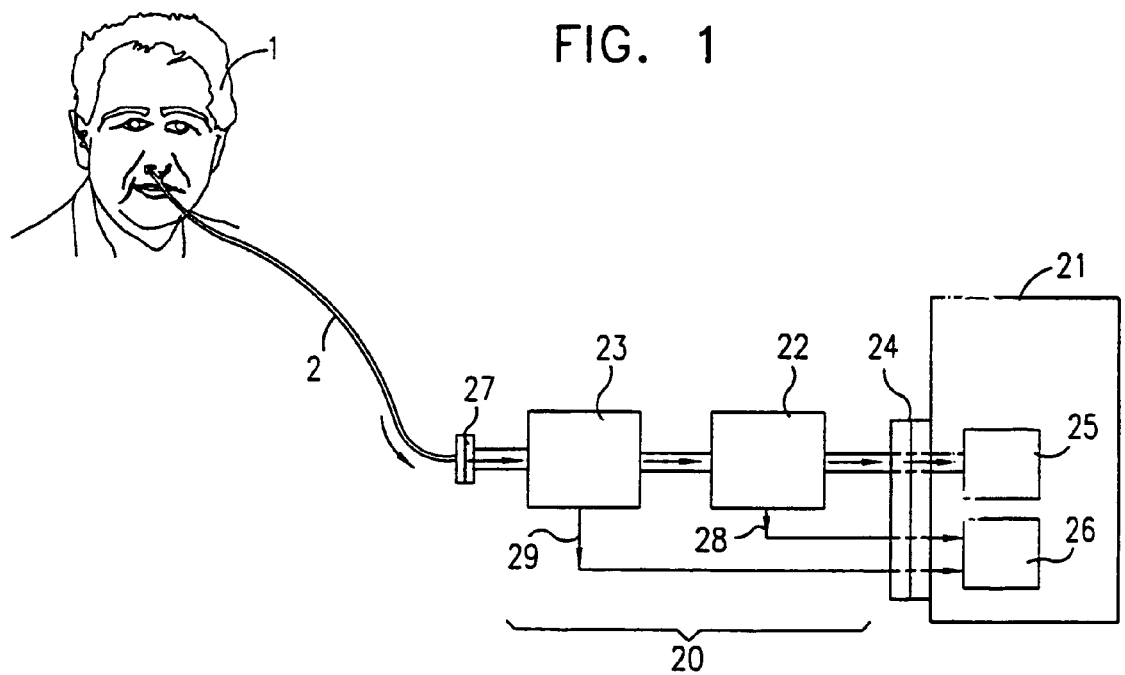
FIG. 1 is a schematic illustration of a gas analyzer calibration checking device, constructed and operative according to a preferred embodiment of the present invention, connected to a breath tester.

Reference is now made to FIG. 1, which illustrates schematically a gas analyzer calibration checking device 20, constructed and operative according to a preferred embodiment of the present invention, connected to a breath tester 21. The device consists of two components, the calibration checking unit 22, and the fluid filter unit 23. The subject 1 is connected to the device by means of a disposable nasal or oral sampling tube 2, into which he breathes. This sampling tube is connected to the filter unit 23 of the device by means of a mating connection 27. The sampling tube is preferably of a simple nasal/oral cannula type, such that it is a low cost disposable item.

The filter unit 23 is attached to the calibration checking unit 22, or is built-into the calibration checking unit, such that the exhaled breath, after any moisture and/or fluids are removed from it, passes through the calibration checking unit 22, into the gas analyzer section 25 of the breath tester 21. The complete gas analyzer calibration checking device 20 is connected to the breath tester by means of a special flange connector 24, whose function is twofold. Firstly, it provides passage of the exhaled breath to be tested into the gas analyzer 25. In addition, it provides one or more of electrical, electronic, optical, magnetic, gaseous and mechanical interfaces, according to the particular embodiment used, between the gas analyzer calibration checking device and the breath tester.

The interface mechanism fitted to the calibration checking unit is preferably constructed such that the first time it is connected to the breath tester, a momentary signal is inputted by means of control line 28 to a controller unit 26 within the breath tester 21, which resets an accumulator unit which counts the number of breath tests performed with each calibration checking unit. The actual count is performed by the breath tester program, and a count could be added to the total, for example, for every occasion that the "Start Test" command is given to the system.

According to a further preferred embodiment of the present invention, the controller unit 26 within the breath tester 12 is operative to start a timing device which accumulates the total time of operation of the breath tester from first connection of a specific calibration checking device. In this embodiment, the criterion for use of a calibration checking device is not the number of tests performed using it, but rather the length of time the breath tester is in operation before a calibration check is considered necessary.

According to another preferred embodiment of the present invention, the signal to reset the test counting mechanism to zero is provided by the entry of the calibration checking gas itself. According to this embodiment, the analyzer is programmed to detect that the gas entering its input port does not have a conventional breath waveform, and the system thus assumes that the gas entering is from a calibration checking procedure. Alternatively, a marker gas could be included with the calibration checking gas, and detected by the gas analyzer.

The filter unit, according to other preferred embodiments of the present invention, may also have an interface control connection 29 to the controller unit 26 within the breath tester 21. This control signal could be used for instance, for warning the user when the filter unit is saturated and no longer efficient. It could even be used to prevent operation of the instrument, even before replacement of the filter is mandated by the elapsed time or number of tests performed. For instance, an accidental ingestion of fluid into the sampling tube from the patient before commencement of the breath test, may render the filter useless for continued use, and without a warning to this effect, the subsequent breath test would be unreliable. This control signal could be preferably generated either by optical detection of the change in color of a moisture absorbing material, such as silica gel, or by the closure of electrical contacts when the accumulated fluid reaches a certain level.

Figure 2A:
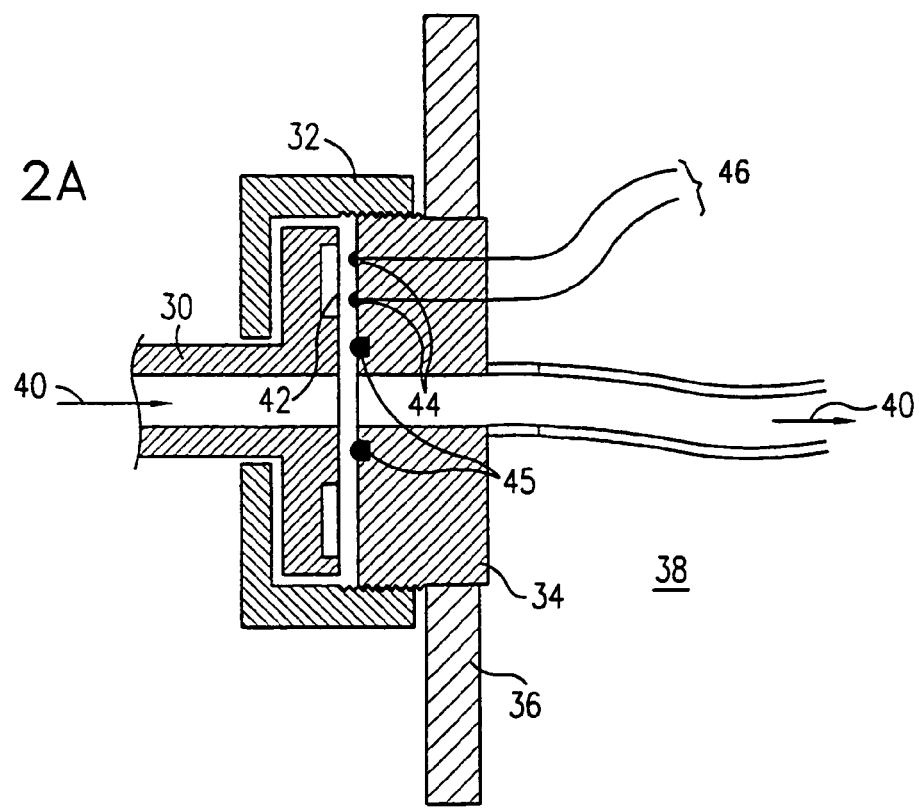
FIGS. 2A and 2B are schematic cut-away illustrations of preferred connector embodiments for interfacing between the gas analyzer calibration checking device, and a breath testing instrument, where

FIG. 2A shows a cut away drawing of a connector incorporating a simple single-use electrical contact interface. The connector flange 30 on the system checker fluid filter device is screwed by means of a knurled nut 32 onto the mating connector flange 34 mounted on the input panel 36 of the breath tester enclosure 38. An O-ring 45 ensures gas tight closure. Once the connector is closed, the gas being analyzed 40 can flow via the calibration checking unit into the gas analyzer of the breath tester. Mounted on a machined hollow or groove in the mating surface of the flange is a thin metallic foil 42, which, on first instantaneous contact with the connector, touches two contact pins 44. This closes an input signal circuit 46 in the controller unit, thereby enabling the commencement of the count of the number of tests performed with that particular calibration checking unit installed. However, on screwing the connector completely home, the foil is ruptured, such that subsequent disconnection and reconnection of the calibration checking unit will not remake the contacts 44, and the clock count cannot therefore be reset to zero using that calibration checking unit connector. In this way, it is impossible for the operator to attempt to use each calibration checking unit beyond the recommended number of times, by attempting to reconnect it anew after expiry.

Figure 2B:
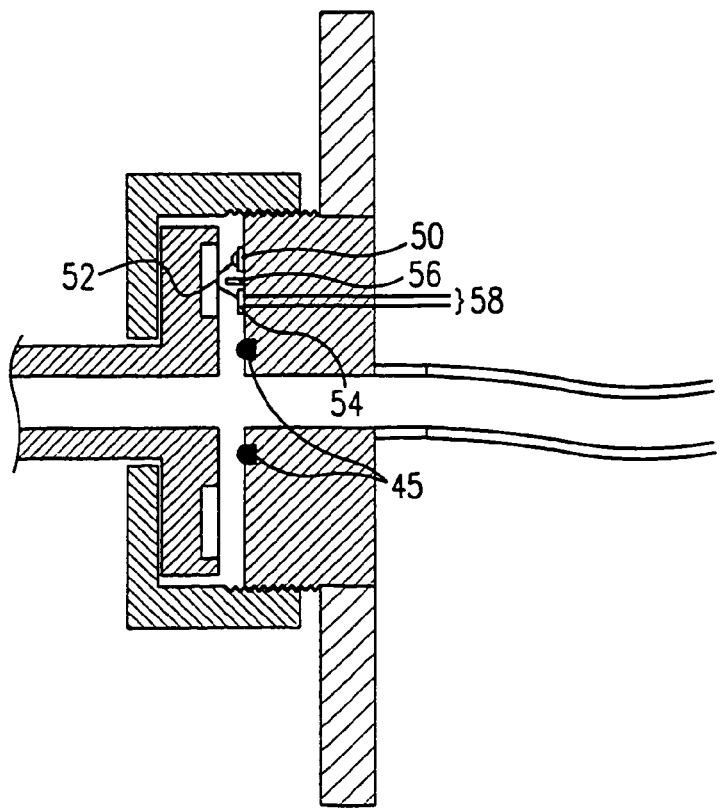

FIG. 2B shows a simple optical interface, which operates in a similar way to the electrical interface shown in FIG. 2A. The trigger signal 58 to commence counting is given by means of the reflection of a light signal transmitted from a source 50 such as a LED, located in the breath tester flange of the interface connector, off a reflective surface such as a metallic foil 52 located in the calibrator flange of the connector, and back to a detector 54 located on the breath tester side. Re-use of the calibration checking unit is prevented by a mechanism designed to degrade the reflective properties of the calibrator connector surface so that after first connection, the unit no longer delivers the required signal if reconnected. In the embodiment shown in FIG. 2B, a projection or pin 56, which tears the reflective foil, fulfills this function. Mechanisms similar to those described in FIGS. 2A and 2B can be proposed using magnetic or mechanical interfaces for ensuring that the calibration checking unit can only be connected once to the breath test unit in an unused state.

Figure 2C:
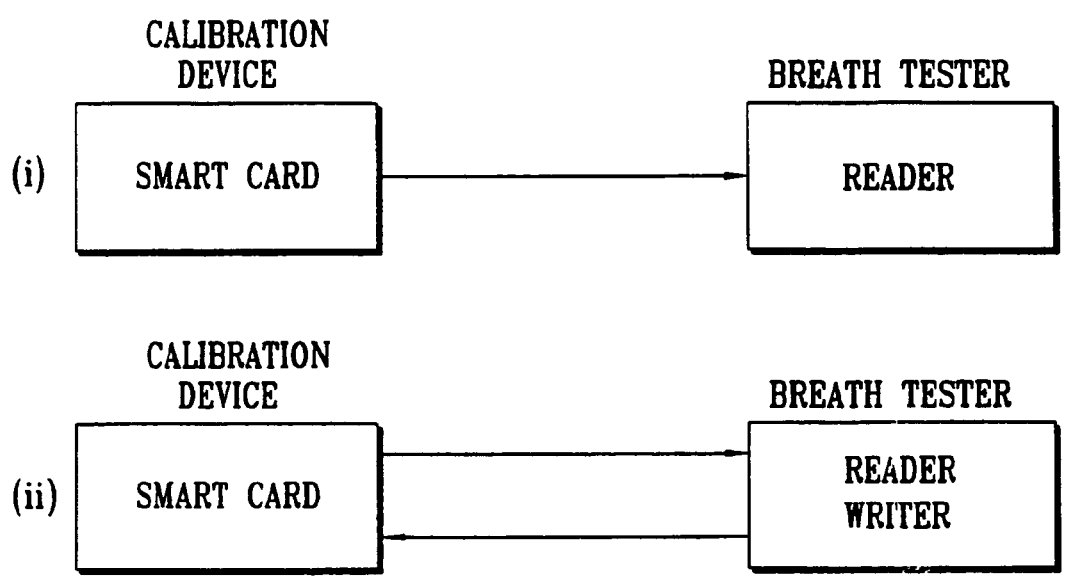
FIG. 2C is a block diagram of the method of interfacing an electronic interface which incorporates an active semiconductor integrated circuit on the calibration checking unit connector.

FIG. 2C now shows block diagrams of methods of interfacing an electronic interface, which incorporates an active semiconductor integrated circuit on the calibration checking unit. A storage device such as a commercially available smart card can be used, to allow an identification of a specific calibration checking unit through appropriate communication. The same storage device could also be used to store information relevant to the calibration checking process such as instrument serial number, calibration date, number of performed tests. The storage of the instrument number could be used to prevent the storage device from being mistakenly used with another instrument, whose calibration had not been checked.

The IC can function in a number of alternative modes. According to one preferred embodiment, shown in FIG. 2C (ii), the count of the number of tests performed by the particular calibrator is performed and stored in the IC itself, by means of routines well known in the art. According to another preferred embodiment shown in FIG. 2C (i), the IC does not play any part in the counting procedure, but simply has a code, which is unique to the particular calibrator unit to which it is attached. On first connection to a breath tester, this code is interrogated, and is stored in the count register of the breath tester. So long as the permitted number of tests with that particular code number has not been exceeded, the breath tester allows another test to be performed.

Communication between the IC in the calibration checking unit and the breath tester can be achieved either by a multipin connector, which is engaged when the calibrator unit is attached to the breath tester, or by means of a radio link, or by any other suitable connection means. In the case of a radio link, there is no need to use a special flange on the calibration checking unit and breath tester.

The above embodiments have been described in terms of an interface designed to commence a count of the number of breath tests that can be performed after each new calibration checking unit has been used. According to yet further embodiments of the present invention, the interface flange can be constructed to provide an interface between the filter unit and the controller circuit, such that the filter unit is the element which actuates the count as to the specified number of breath tests permissible before stopping operation of the tester until filter replacement is made. The design of the flange could then be identical to that shown in FIGS. 2A and 2B, except that the circuit closing elements are associated with the filter unit.

According to yet another preferred embodiment, the filter unit can be constructed to provide a warning signal to the controller circuit through the interface flange, such as is described above, if the absorbed fluid rises to a level above which the filter no longer operates satisfactorily, or if the moisture absorber becomes saturated, even before the permitted number of breath tests has been performed with it. In this way, the filter function is doubly protected, both in terms of frequency of replacement, and in terms of efficacy.

Figure 3:
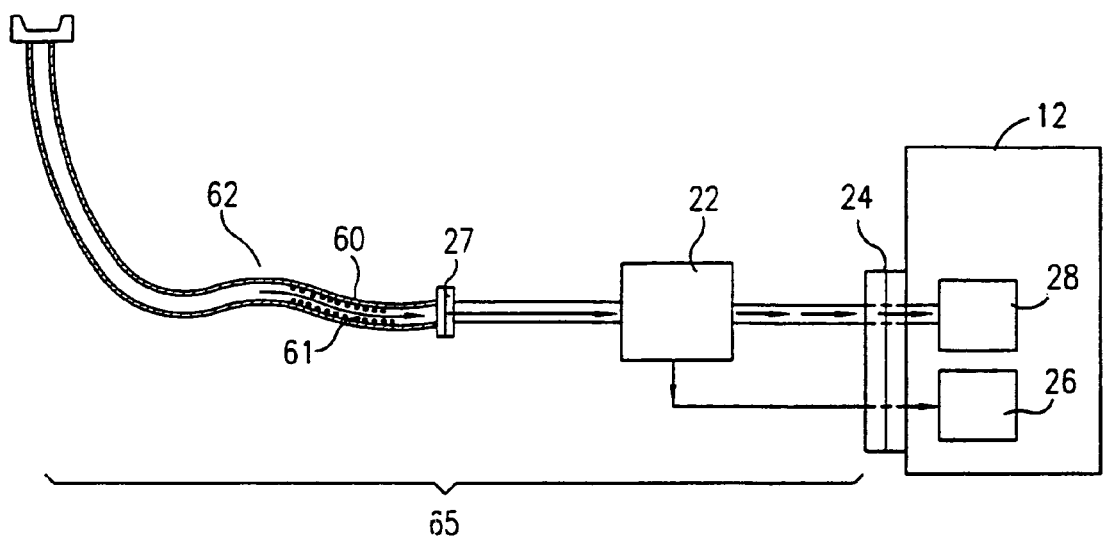
FIG. 3 is a schematic representation of another preferred embodiment, in which the filter function is performed by means of a dedicated section of the disposable oral/nasal cannula sampling tube, which has built-in filtering properties.

Reference is now made to FIG. 3, which illustrates schematically a calibration checking fluid filter device 65, constructed and operative according to another preferred embodiment of the present invention. According to this embodiment, the filter unit is of low cost, simple construction, such that it is intended to be an built-in part of the sampling tube 62, and is, therefore, disposable like a regular sampling tube. In FIG. 3, the filter is a section 60 of the sampling tube, designed to dry the gas by absorbing moisture, such as by coating the inside walls 61, or partially filling the volume, with a water absorbent material such as silica gel. In this respect, the "filter" does not fulfill the generally accepted functions of removing bulk moisture, and should thus strictly be called a dryer and not a filter. For every new breath test, a new sample line with dryer section is used, being connected to the calibration checking unit by means of a connection 27. The electronic interface for preventing operation of the instrument is then operative only from the calibration checking unit. As in the previous embodiments described, the calibration checking unit 22, is preferably interfaced with the breath tester 21 by means of a "smart" connector 24, which allows control of the number of breath tests performed with each calibration checking unit.

If a capnographic measurement is to be made of the breath exhaled by the patient, it is important that the waveform of the breath be maintained in passage through the filter unit, to ensure an accurate capnographic measurement. The preferred embodiment shown in FIG. 3 fulfills this requirement, since the gas flow down the sample tube flows in a smooth laminar manner without any significant obstructions or perturbations, and without any pockets or corners of void volume which could disturb the waveform.

Figure 4:
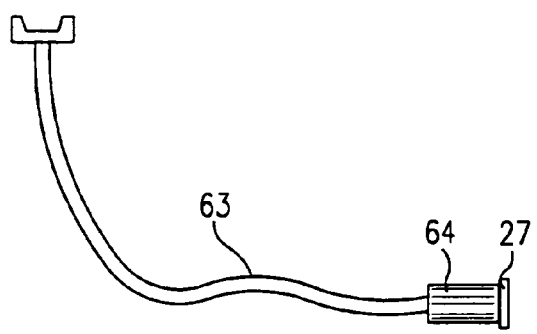
FIG. 4 is a schematic illustration of a sampling filter line whose filter section is preferably one of those described in U.S. Pat. No. 5,657,750, incorporated by reference in its entirety.

Alternatively and preferably, any of the true fluid filtering devices described in U.S. Pat. No. 5,657,750 could also be used for this purpose. The filters disclosed therein are constructed so as to avoid significant disturbance to the waveform. FIG. 4 illustrates a sampling filter line 63 whose filter section 64 is preferably of the type disclosed in U.S. Pat. No. 5,657,750. The sampling filter line is attached to the calibration checking unit by means of the flange 27.

According to another preferred embodiment of the present invention, the filter unit can be constructed with a color marker which changes color when the filter is saturated, thus providing the user with visible warning that the filter should be replaced, even before the permitted number of breath tests has been performed with it, and the instrument interface would prohibit its further use.

Figure 5:
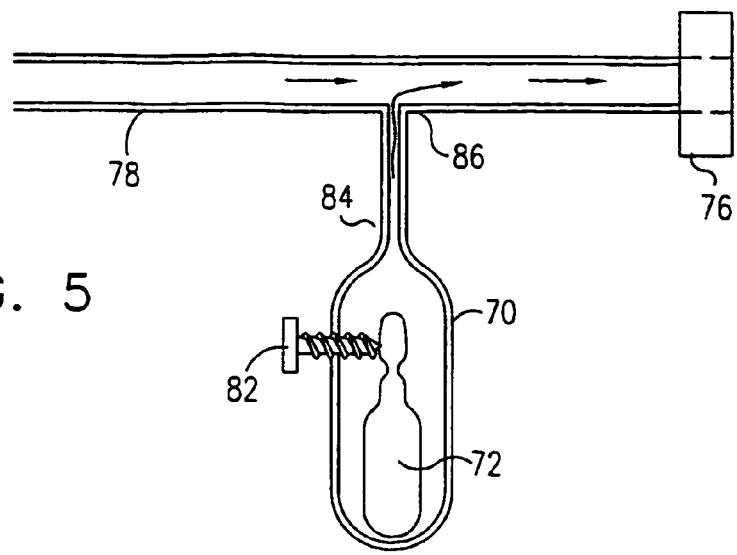
FIG. 5 is a cut-away schematic diagram of an embodiment of a calibration checking unit, showing a glass ampoule containing premixed calibration gases.
Figure 6A:
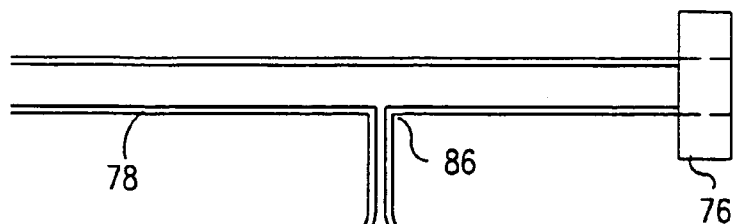
FIGS. 6A and 6B are cut-away schematic diagrams of two preferred embodiments of calibration checking units, with two glass ampoules, each containing premixed calibration gases.
Figure 6B:
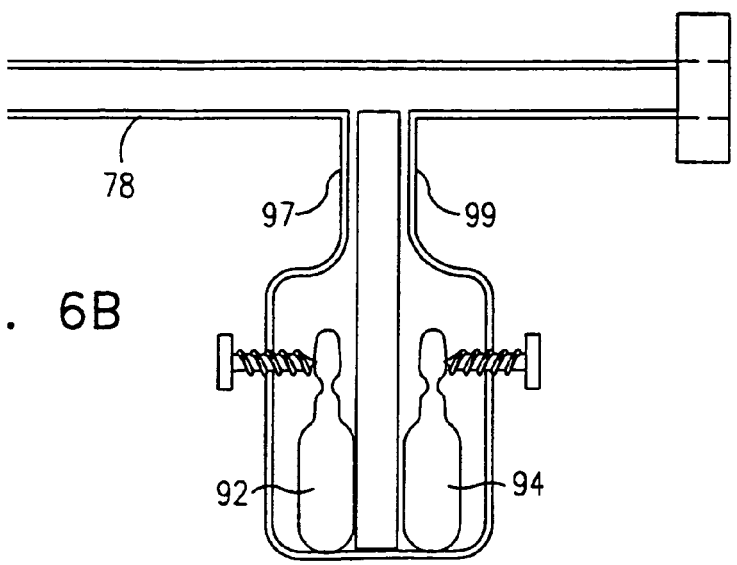

Reference is now made to FIG. 5 and FIGS. 6A and 6B, which show cut-away schematic diagrams of calibration checking units, constructed and operative according to preferred embodiments of the present invention. The calibration checking units incorporate one or more containers of a premixed calibration checking gas, and can be used in any of the calibration checking devices described in the previous embodiments, regardless of which filter configuration is used. With one exception, the calibration checking units are in interactive control contact with the gas analyzer control system, such that they either cannot be used without transmitting a start signal to the control system of the gas analyzer, or they themselves are actuated by means of a control signal received from the gas analyzer control. The one exception is the embodiment wherein detection of the calibration checking gas itself by the gas analyzer provides the start signal for the counting or timing process for use of that particular calibration checking device.

It is understood that the embodiments shown in FIG. 5 and FIGS. 6A and 6B are schematic only, and serve only to illustrate the operational method. In practice, the shape, dead volume, method of gas release and other details are suited to the gas containers used, such as is described hereinbelow in the embodiments shown in connection with FIGS. 13 to 16.

The operation of the calibration checking units is described for use with a breath test for the detection of changes in the level of $^{13}CO_2$ in the patient's breath, after ingestion of a $^{13}C$-labeled substrate. It is to be understood, however, that the units can be equally well applied for use in breath tests with other isotopically replaced atoms, such as nitrogen-15 and oxygen-18.

In the embodiment shown in FIG. 5, the calibration checking unit housing 70 incorporates a glass ampoule 72 containing the calibration checking gas, though it could be provided in any form of container capable of being hermetically sealed yet easily opened on demand, such as a metallic cylinder with a foil seal or a depressable check valve. The calibration checking unit is connected through a narrow bore tube 84 by means of a T-connector 86 into the sampling line 78, which is connected to the breath tester preferably by means of an interface connector 76, such as those described in relation to FIGS. 2A to 2C. In the preferred embodiment shown, a plunger 82 is incorporated in the wall of the calibration checking unit housing 70, such that when the plunger is depressed, the ampoule is broken and the calibration checking gas mixture released. Though shown otherwise for clarity, the calibration checking unit housing 70 and the glass ampoule 72 should be constructed in such a way as to leave a minimum of dead space between them, to avoid diluting the released calibration checking gas with residual gas in the dead space.

The long narrow bore tube 84 now acts as a flow restrictor to prevent the calibration checking gas from being released too rapidly into the sampling line 78. This ensures that no overpressure effects are produced in the sampling line. An overpressure may overcome the effect of the system vacuum pump located in the breath tester, and allow some of the calibration checking gas to escape from the system towards the patient's end of the sampling line. Furthermore, the delivery of the calibration checking gas in sidestream fashion to the sampling line via a T-connector avoids any significant disturbance to the breath waveform, since the small entry hole and the long narrow bore connection tube do not present any appreciable perturbation or void volume to the sample gas flow. This is very important for use with any instrument in which capnographic measurements must be made, in order to avoid damage to the waveform of the breath.

Alternative and preferable methods of releasing the calibration checking gas include solenoid plungers electrically operated on demand by the breath tester calibration checking program, or mechanical needles or projections incorporated into the breath tester input flange, which cause mechanical breakage of the gas container seal or depression of a check valve on the calibration gas cylinder as the calibration checking unit flange is screwed home onto the breath tester flange. Preferred examples are described hereinbelow, and provide more specific details of the schematic examples outlined hereinabove. The operating mechanism of any gas release device not actuated by the control system of the gas analyzer, can be constructed to send its own "calibration check start" control signal when actuated, to the gas analyzer.

When the time comes to perform a system check or a calibration check, a new calibration checking unit, with or without a filter unit attached, is connected to the breath tester. No subject is connected to the sample tube, since natural air from the environment is required for the system checking procedure. The calibration check gas is released, either by operation of the plunger, or by another of the methods mentioned above, or by any other suitable method, and the calibration checking gas allowed to mix with the incoming stream of ambient air, and to enter the breath tester.

The ampoule contains a known volume of $CO_2$ such that, with the flow rate ingested by the breath tester, the final percentage of $CO_2$ in the ingested gas is of the order of 5%, which is just above the chosen concentration of operation of the gas analyzer. This level can be achieved, for instance, by defining the volume of gas in the ampoule such that when diluted by the known flow rate of the instrument, the correct concentration is achieved, or by means of an intermediate chamber system, such as that described in the above-mentioned PCT Publication No. WO 99/14576. Since the volume of the intermediate cell described in PCT Publication No. WO 99/14576 is of the order of 300 ml., then the ampoule should have a volume of the order of 15 ml of 100% $CO_2$ at atmospheric pressure, to ensure that a 5% $CO_2$ intermediate cell concentration is reached. If a typical flow rate of 250 ml/min. is ingested, the chamber should be full of gas ready for the measurement in a little over 1 minute.

It should be emphasized here that it is not necessary to achieve the exact target $^{12}CO_2$ concentration level for performing a calibration check. The important factor for achieving accurate calibration is the isotope ratio present in the gas. This is why it is possible to use a small ampoule of calibration checking gas for dilution with the ambient flow, instead of requiring a monitored flow of accurately diluted gas from the ampoule alone.

The carbon dioxide calibration gas used contains a small added volume of $^{13}CO_2$ above the level of the ambient air. This added volume is calculated to be sufficient to cause the isotopic ratio of $^{13}CO_2$ in the carbon dioxide entering the breath tester to show a slight increase over that expected from a patient showing a negative response to the breath test. Typically, a value of 5δ is used for the calibration checking procedure, where δ is 10 parts per million. A value of 5δ enables a clear calibration check to be made, yet at a level close to the typical detection levels demanded of the breath tester in normal use.

The calibration check is performed by the use of a stream of flowing ambient air, which generally contains no more than 1000 ppm of $^{12}CO_2$ and 10 ppm of $^{13}CO_2$, to which is added a small volume of the calibrating gas at its full concentration level. As an alternative, an ampoule full of ready mixed calibration checking gas at the correct dilution could be used, containing a sufficiently high volume of gas to fill the complete system. This, however, would make the calibration check more costly, and would also result in a sudden rush of gas into the system as such a large volume of gas is released, which would make it difficult to operate at ambient pressure, without allowing the overpressure to dissipate, thus requiring an even larger volume of calibration checking gas. Furthermore, a container with 300 ml of gas, even if somewhat compressed, would occupy valuable space in such an instrument, compared with a 9 ml sample.

FIG. 6A now shows an additional preferred embodiment for performing the instrument calibration check, in that the calibration checking unit housing 90 incorporates two ampoules 92, 94 of calibration checking gas. In the first ampoule 92 is contained a quantity of natural carbon dioxide, whose volume is such that its release into the flow of air through the system will result in the predetermined percentage of $CO_2$ for the measurement system to operate optimally. The level of $^{13}CO_2$ contained is that of the sample used, and the release of the gas from inside the ampoule, such as by operation of the first plunger 96, or by any of the methods described hereinabove, enables a calibration check of the base line of the measurements, against which all future measurements are made. The second ampoule 94 contains natural carbon dioxide calibration checking gas containing a small added volume of $^{13}CO_2$ in comparison to the gas in the first ampoule 92. This additional volume is sufficient to cause the percentage of $^{13}CO_2$ in the carbon dioxide entering the breath tester to be slightly higher than that of the baseline, which contains $^{13}CO_2$ at a typically naturally occurring level. Typically, a value of 20δ is used. Once the baseline calibration check has been performed, the second ampoule 94 is opened by means of plunger 98, and a calibration check at the pre-chosen 20δ level is performed. This embodiment therefore allows the measurement span of the breath tester to be correctly calibrated, in addition to the point calibration check performed in the single ampoule embodiment. In use, the frequency of performance of a calibration check, will be determined by local conditions of use of the instrument.

FIG. 6B is a schematic drawing of an embodiment similar to that of FIG. 6A except that the gases from the two ampoules are preferably conveyed to the sampling line 78 in separate tubes 97, 99, in order to avoid any mixing of residual gas remaining from the first ampoule 92, when the second ampoule 94 is broken. Such mixing could interfere with an accurate calibration.

For use in the complete calibration checking device of the present invention, the calibration checking unit described in this embodiment may be combined with any of the interfaces or moisture filters described in the previously mentioned embodiments brought hereinabove.

Reference is now made to FIGS. 7A and 7B, which illustrate schematically the operational concepts which are the basis of the calibration checking methods according to further embodiments of the present invention. FIG. 7A schematically shows a representation of a source of calibrating gas 132, shown for the preferred example of a carbon dioxide breath test, connected by means of a tube 130 to the interface connector 76, where the gas is input to the breath tester. The source 132, can preferentially be either one or more containers of calibrating gas with known concentrations and isotopic ratios, or a calibration checking device as described hereinbelow, capable of generating samples of calibrating gas of known concentration and isotopic ratio from a reservoir, or alternatively, even an accumulated sample of the breaths taken from subjects either before ingestion of the isotopic labeled substrate, or from subjects whose breath tests show them to be negative, or alternatively, an accumulated sample of breath from a single subject showing a positive result of his breath test. In all of these cases, the breath tester checking system is operative to take the sample of gas, and to dilute it down by means of the intermediate chamber system in the breath tester, into a number of different samples, each of different concentration, but with the same isotopic ratio, since each sample originated from the same, single, calibration sample of higher concentration. The isotopic ratio of each of these samples is then measured in the breath tester. FIG. 7I shows a schematic graph of results typically obtained from such a series of dilutions and measurements. The change in isotopic ratio from the average value, marked as Δδ=0, shows a small ±3δ cyclic variation about the average value. Though ideally, a straight line at the average value should be obtained, the realities of experimental and measurement noise are such that the typical result shown in FIG. 7B is acceptable as the output of a reasonably well calibrated instrument. If the curve in FIG. 7B were to show a monotonic dependence on $CO_2$ concentration, this would be symptomatic of a systematic calibration error in the instrument, probably arising from a shift in the absorption curve parameters used to convert luminous transmission into gas concentration.

According to other preferred embodiments of the present invention, the breath tester is capable of performing an independent system check of all of its major functions, including a system calibration check, by means of a pseudo-breath test on samples of calibrating gas. The pseudo-breath test is accomplished using a breath simulator device, which generates a breath sample with its major characteristics similar to those expected in the normal operation of a real breath test. The characteristics which the device simulates are:

(a) flow rate,
(b) maximum and minimum levels of total $CO_2$ concentration,
(c) $^{13}CO_2/^{12}CO_2$ ratio, and
(d) respiration rate.

The order of magnitude of the values of these parameters of the samples which the breath simulator should preferentially provide are:

(a) Approximately 250 ml/min.
(b) Samples of approximately 0 and 5% $CO_2$.
(c) Samples with approximately natural ratio level and 5δdeviation therefrom.
(d) Approximately 15 $min^{-1}$.

Several methods of generating and using such a calibrating gas flow device have been mentioned hereinabove. One of the most convenient devices, according to a further preferred embodiment of the present invention, utilizes a tube of porous material which behaves as a diffusive membrane. Because of the small size of the porous holes, 0.5 μm or less, there is very little bulk mechanical flow of gas through the wall, but gases, including $CO_2$ can pass through with a relatively high diffusion rate. As an alternative to the non-selective diffusive membrane, a selective membrane with a preferred rate of penetration of carbon dioxide can also be preferably used. One example of such a material is RTV silicone, which has a diffusion rate for carbon dioxide about 8 times higher than for nitrogen, though a much small difference in the diffusion rate for the $^{13}CO_2$ and $^{12}CO_2$, commensurate with the differences in their molecular weights. An advantage of the use of a selective membrane over a porous tube is the comparative lack of interference from the reverse diffusion of air, compared with carbon dioxide.

It should be understood that though these preferred embodiments are described in terms of diffusion of isotopes of carbon dioxide, they are equally applicable to preferential diffusion of any gaseous isotopic cleavage product which appears in the exhaled breath of a patient. Each gas breath tested will in general require its own different porous material, to provide a suitable diffusion ratio for the gases to be measured.

Reference is now made to FIG. 8, which schematically shows a preferred embodiment of such a porous tube device. The gases flow through the tube from one end 150 to the other 152. The wall material 154 is made of a porous material chosen such that the gases flowing within, including carbon dioxide, undergo diffusion 156 out through the wall. If the wall material is a selective membrane, then the carbon dioxide diffuses through it at a significantly higher rate than other gases. If it is a diffusive membrane, the carbon dioxide diffuses through it at a rate, not very different from that of other gases of similar molecular weight, such as oxygen and nitrogen. Whichever embodiment is used, the wall thickness of the porous section, its length and the flow rate of gas through it can be conveniently and preferentially chosen such that in passage down the porous section, the desired proportion of the carbon dioxide content diffuses out.

However, because of the different molecular weights of $^{13}CO_2$ and $^{12}CO_2$, the $^{13}CO_2$ diffuses out more slowly than $^{12}CO_2$ and the result is a small enrichment of the $^{13}CO_2$ level in the gas after its passage through the porous tube. The diffusion constant is inversely proportional to the square root of the molecular weight, M, of the diffusing molecule. By means of mass diffusion calculations, it can be shown that the relative change ΔR in the isotopic ratio R of $^{13}CO_2$ to $^{12}CO_2$ in passage of the gas down such a porous tube is given by a functional expression of the general form:

$$\Delta R = 1000*(R_{out}-R_{in})/R_{in} = f\{\Delta(^{12}CO_2), (^{12}CO_2)_{in}, D(^{12}CO_2)/D(^{13}CO_2)\}$$

where:
$R_{in}$=isotopic ratio at input to tube
$R_{out}$=isotopic ratio at output of tube
$D(^{12}CO_2)$=diffusion coefficient of $^{12}CO_2$ α $\sqrt{M(^{12}CO_2)}$
$D(^{13}CO_2)$=diffusion coefficient of $^{13}CO_2$ α $\sqrt{M(^{13}CO_2)}$
$\Delta(^{12}CO_2)$=change in percentage of $^{12}CO_2$ in passage down the tube, and
$(^{12}CO_2)_{in}$=percentage of $^{12}CO_2$ at the tube input.

Figure 9:
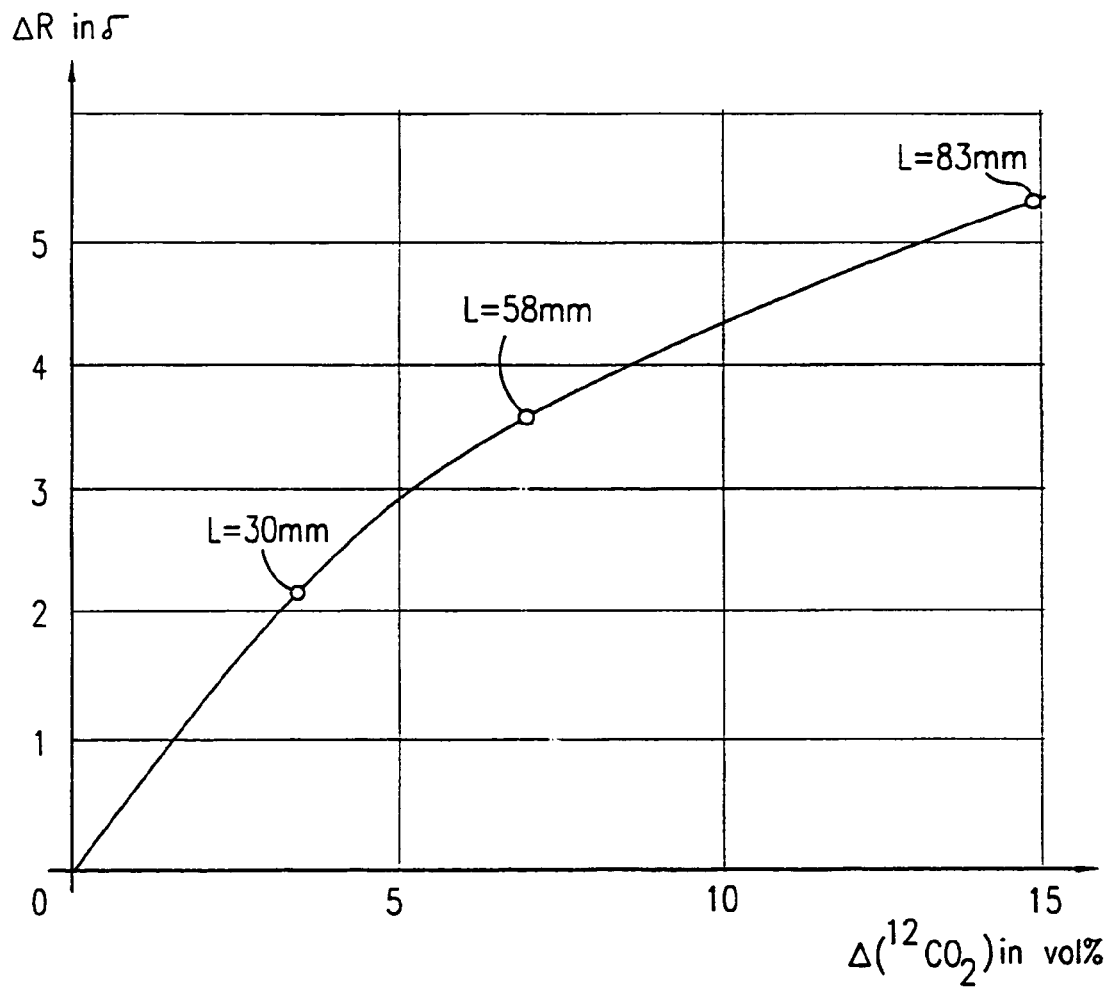
FIG. 9 shows a graph of experimental results of the change in isotopic ratio obtained in the passage of carbon dioxide down a porous tube of the type shown in FIG. 8, as a function of the $CO_2$ concentration and of the length of the tube used.

Reference is now made to FIG. 9, which shows a graph of experimental results of the change in isotopic ratio obtained in the passage of carbon dioxide down a porous tube, according to preferred embodiments of the present invention, as a function of $\Delta(^{12}CO_2)$ and of the length of the tube used. The tube is preferably constructed of a polypropylene material and has an inner diameter of 1.4 mm, an outer diameter of 2.2 mm, and an average pore size of 0.37 μm. The flow rate of gas is approximately 250 ml/min. The abscissa of the graph depicts $\Delta(^{12}CO_2)$, the change in percentage of $^{12}CO_2$ in passage down the tube, and the ordinate is ΔR, the resulting fractional isotopic increase in the ratio of $^{13}CO_2$ in the gas after passage through the porous tube. The results are plotted for the situation which results in a 5% concentration at the outlet. The length, L, of porous tube used is marked beside each point obtained.

As an example of the use of this graph in the selection and operation of such a porous filter, in order to obtain a 5% concentration $CO_2$ sample flow with a $^{13}CO_2$ isotopic ratio decrease of approximately $5\times10^{-5}$ i.e. 5δ, the input concentration of carbon dioxide must be approximately 18%, and the length of tube used approximately 80 mm. This change of 5δ in the level of $^{13}CO_2$, is close to the lower limit of detected level changes which enable a positive diagnosis to be made using the breath tester. A tube of such dimensions is thus suitable for use in supplying a sample of gas, of known concentration and flow rate, and with a known isotopic ratio change, close to practically detected threshold level changes, for use as a calibrating element.

Though the embodiment shown in FIG. 8 is inexpensive to construct and simple to operate, the presence of ambient air at the outer wall of the porous tube results in one disadvantage in its operation. Because of the likely lack of positive ventilation around the tube, there may be an accumulated carbon dioxide content in the air around the tube, thus creating a different carbon dioxide gradient across the tube wall and a change in the rates of diffusion of the isotopic gases outwards. This will thus cause a change in the calibration factor of the tube.

Figure 10:
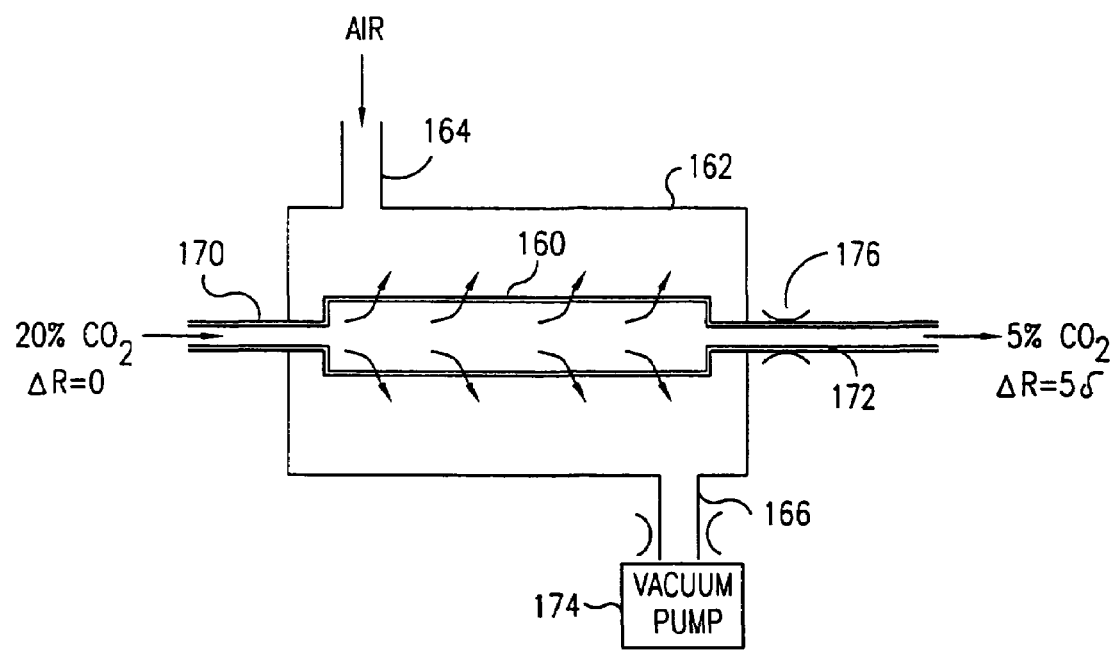
FIG. 10 illustrates a double-stream porous tube calibrator, in which the rate of diffusion is more closely controlled than in the embodiment shown in FIG. 8.

Reference is thus now made to FIG. 10, which schematically illustrates an alternative and preferred embodiment of the porous tube device according to the present invention, wherein the above-mentioned problem is overcome and the rates of diffusion are more closely controlled. This embodiment is known as the double-stream porous tube calibrator. The porous tube 160 is enclosed within an outer housing 162, through which air flows, from the outer housing input 164 to the outer housing output 166. A steady air flow is maintained by means of a vacuum pump 174. The air flow must be sufficient to avoid the generation of an appreciable carbon dioxide gradient across the wall, which would affect the diffusion rate of carbon dioxide through it. A flow of carbon dioxide, as in the embodiment of FIG. 8, passes through the porous tube, from its entrance 170 to its exit 172. The carbon dioxide preferentially originates from a gas source with 20% carbon dioxide, and a flow restrictor 176 determines the flow rate.

In use, carbon dioxide from the porous tube 160 diffuses out through the tube wall and into the inside volume of the outer housing, from where it is removed by the flowing air. The quantity of carbon dioxide diffusing out is determined, as in the simple embodiment shown in FIG. 8, by the tube dimensions and the pore sizes. After its passage through the porous tube, the $^{13}CO_2$ enriched gas flow is used as the calibration checking gas of known concentration, flow rate and amended isotopic ratio, thereby simulating a real breath test sample. The advantage of this embodiment over the simpler embodiment shown in FIG. 8 is that the rate of diffusion across the porous tube wall is now independent of environmental conditions, since both sides of the wall have known and controlled conditions.

Figure 11:
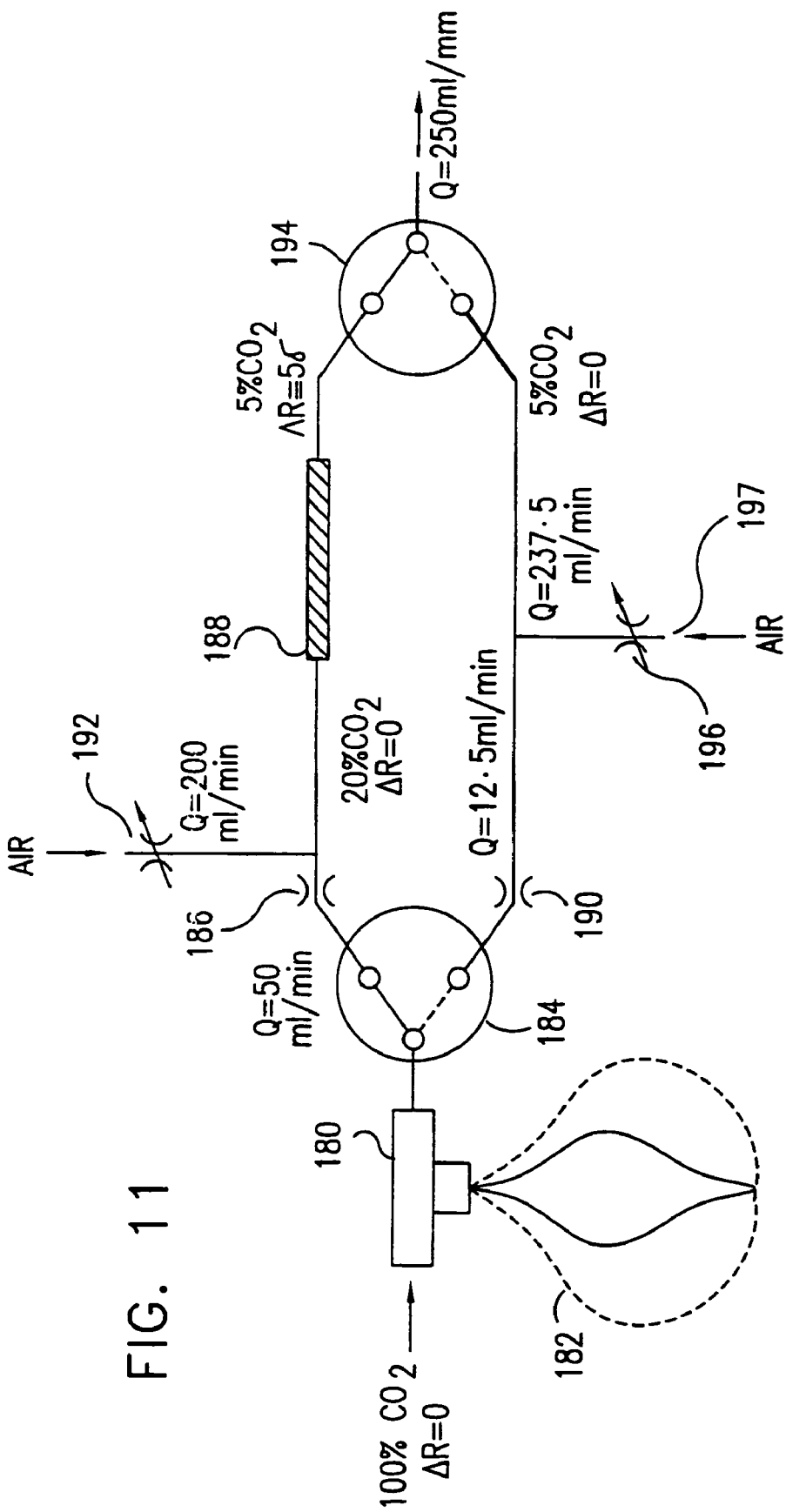
FIGS. 11 and 12 which schematically show different embodiments of flow systems with dynamic isotopic ratio control, for supplying a breath tester with calibration gas samples, incorporating the porous tube devices depicted in FIG. 8 and FIG. 10 respectively.
Figure 12:
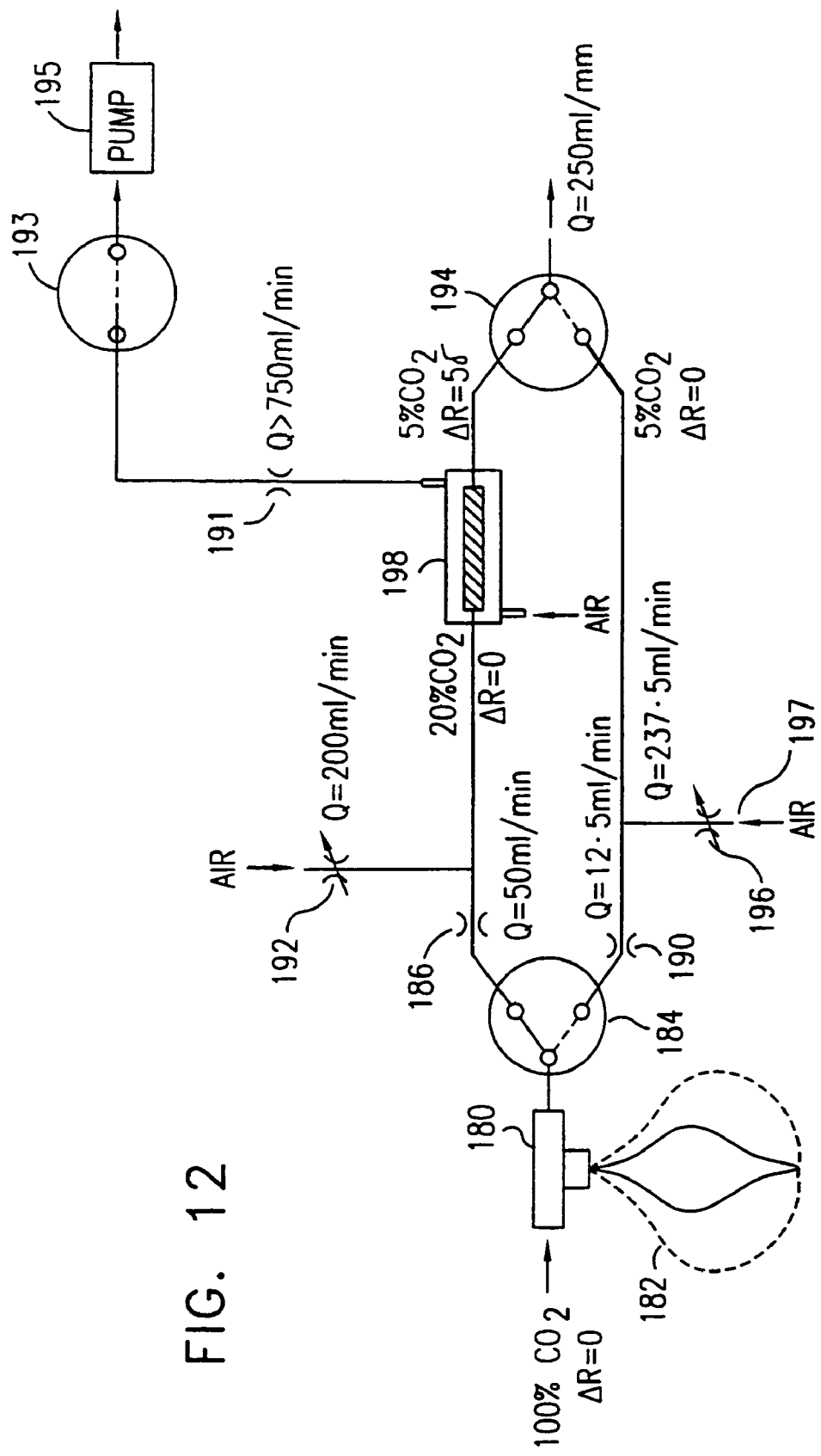

Reference is now made to FIGS. 11 and 12 which schematically show the porous tube devices depicted in FIGS. 8 and 10 respectively, incorporated, according to preferred embodiments of the present invention, into flow systems with dynamic isotopic ratio control, for supplying the breath tester with calibration gas samples. In both of the embodiments shown, the carbon dioxide is supplied in containers filled with 100% carbon dioxide, and at a pressure of up to 5 bar. The use of 100% carbon dioxide enables the smallest feasible volume of gas container to be used, thereby increasing user convenience.

In FIG. 11, the carbon dioxide is input to the flow system through a T-piece 180, to the third arm of which is connected an inflatable bladder 182. The function of this bladder is to regulate the flow of the carbon dioxide into the system when the cylinder or container, typically pressurized at 5 bar, is connected. The initial input flow of higher pressure gas inflates the bladder, which then slowly deflates as it drives the gas gradually into the flow system. In addition to the effect of the expanded bladder, the breath tester itself is fitted with a vacuum pump which provides suction for inputting the gas samples. The carbon dioxide then reaches a switchable solenoid valve 184, which directs the carbon dioxide either into the upper arm via a flow restrictor 186 to the porous tube 188, or into the lower arm, known as the by-pass arm, also through a flow restrictor 190. Before it enters the porous tube 188, the carbon dioxide content of the gas in the porous tube arm is diluted by means of air, input into that arm through a variable flow restrictor 192. This air is preferentially obtained from the line used for inputting the breath samples, since air drawn in through that line undergoes a drying process by means of a fluid filter located in the line. Means are provided for sensing when a nasal cannula is attached to the input connector, and disabling the calibration procedure, to ensure that the porous tube calibrating device is not actuated when a patient is connected to the instrument, since in that situation, the patient's breath rather than air may be ingested.

The single flow porous tube device is able to provide an isotopic divergence as high as 5δ only if the concentration drop through it is limited to about 25%. Consequently, in order to achieve 5% concentration at the output, the carbon dioxide concentration must be reduced before entry into the porous tube device to approximately 20%. The flow restrictor 192 is adjusted to provide the exact concentration of carbon dioxide needed at the input to the porous tube 188. By selection of the correct type of porous tube, the gas, after passage through it, contains 5% carbon dioxide with a 5δ isotopic ratio deviation from the reservoir gas. This calibrating sample is then routed through an output solenoid valve 194, for entry into the breath tester during the calibration procedure.

Gas directed by the solenoid valve 184 into the by-pass branch, passes through the flow restrictor 190, and is then diluted down to 5% concentration by means of air which is admitted through an adjustable restrictor 196. Since the gas in the by-pass arm does not undergo any preferential diffusive process, the isotopic ratio remains unchanged, and ΔR=0. The switchable solenoid valve 194, in its alternate position, routes this gas sample to the breath tester for use in the calibrating procedure.

The flow rate of the gas mixtures is preferably maintained at 250 ml/min, as typically used by the breath tester. For the 5δ sample from the porous tube branch, the settings of flow restrictors 186 and 192 jointly maintain this desired flow rate, with 50 ml/min carbon dioxide flow, and 200 ml/min. air flow. For the zero ΔR sample in the by-pass arm, this desired flow rate is determined by the settings of flow restrictors 190 and 196, with 12.5 ml/min carbon dioxide flow, and 237.5 ml/min air flow.

The flow system shown in FIG. 12 is operationally similar to that shown in FIG. 11, except that a double stream porous tube device 198, such as that in FIG. 10 is used instead of the single flow porous tube of FIG. 8. Components of FIG. 12 with functions identical to those of FIG. 11, are identically labeled. The flow rate of the flushing air in the outer housing of the double stream porous tube device 198 is set at the preferable desired level of more than 750 ml/min by means of the flow restrictor 191. A solenoid valve 193 is located before the exit from the device to the vacuum pump 195, in order to isolate the device from the pump action except when a calibration is required.

Figure 13:
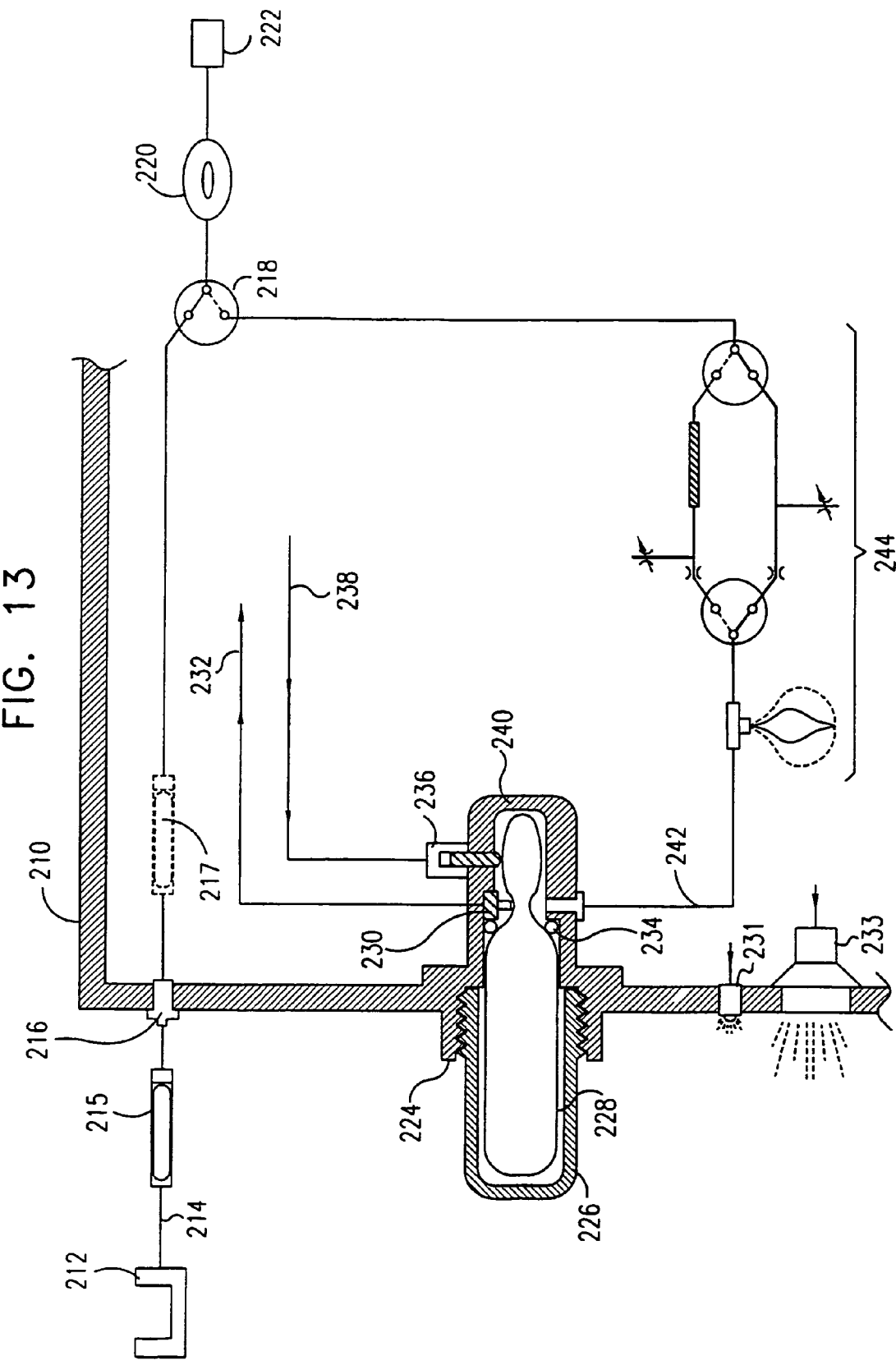
FIG. 13 schematically illustrates a preferred embodiment for the mechanical incorporation in a breath test instrument, of a single-flow porous tube device of the type shown in FIG. 11, for the execution of a calibration checking procedure.

Reference is now made to FIG. 13 which schematically illustrates a preferred embodiment for the mechanical incorporation of a single-flow porous tube device for the execution of the service or operator calibration checking procedure in a breath test instrument 210. During normal clinical use, the patient's breath samples are collected, preferentially by means of a nasal cannula 212, and conveyed by means of a sample tube 214 and via a fluid filter 215, for removal of excessive moisture and fluids, to the input connector 216 of the breath tester. Alternatively and preferably, an additional fluid filter 217 can be installed inside the instrument in the line conveying the breath sample gas from the input connector ultimately to the gas analyzing system 222. The typical breath collection system provides samples with a flow rate of 250 ml/min, and at a pressure of 50 mbar below ambient pressure, generated by means of a vacuum pump incorporated into the gas analysis system 222. During normal use for breath analysis, these breath samples are routed to the gas analyzer system 222 via the input capnographic sensor 220, by means of a switchable solenoid 218.

Disposed in the front panel of the breath tester is a calibration input connector, preferably in the form of an internally threaded port 224, adapted to receive the externally threaded calibration gas housing 226. According to one preferred embodiment of this calibration gas unit, the calibration gas is contained in a glass ampoule 228 disposed within the housing. The ampoule preferably contains 100% carbon dioxide at a pressure of up to 5 bar, as explained hereinabove. The total volume of calibration checking gas required is 40 ml at STP, which is equivalent to 8 ml at the ampoule pressure of 5 bar. As a result, the gas calibration checking unit is of a conveniently small size. This drawing of the ampoule and its housing shows in more detail the general concept first shown in FIG. 5.

According to another preferred embodiment of the present invention, as the calibration checking gas housing is inserted, a sensor mechanism 230 in the receiving housing detects the presence of the calibration checking gas unit, and transmits a signal 232 to the breath tester control system to enable the calibration checking procedure system. The sensor can preferably be a microswitch, an optical or capacitive sensor, or any other suitable detection device. Alternatively and preferably, the calibration checking procedure may be initiated by means of an operator command from the instrument control panel.

When the calibration checking gas housing is screwed home, an internal gas tight enclosure is formed by means of an O-ring 234, and the calibration checking gas flows into this enclosure when the neck of the ampoule is broken to release the calibration checking gas. The gas tight enclosure is preferably constructed to leave a minimum of dead space around the ampoule neck, so that the ampoular contents are not unduly diluted by residual gas within the gas-tight enclosure. In the preferred embodiment shown, the ampoule is broken by means of a solenoid operated electromechanical mechanism 236 actuated by a signal 238 provided by the breath tester when the calibration procedure is invoked. The ampoule may also be broken automatically by mechanical or other means. In the embodiment shown in FIG. 13, in addition or as a preferred alternative to the solenoid operated mechanism 236, an automatic breakage mechanism is shown in the form of a mechanical stop 240, which breaks the glass neck of the ampoule when the calibration checking gas housing is screwed right home.

An internal tube 242 conveys the calibration checking gas from the gas tight housing to a porous tube flow system 244. The porous tube flow system is preferentially of the type depicted in FIG. 11, though a type such as that depicted in FIG. 12, or any other equivalently functioning type could equally and preferentially be used. The calibration checking gas samples from the porous tube flow system are conveyed to the switchable solenoid valve 218. When a calibration checking procedure is enabled by the breath tester control system, the solenoid valve 218 is switched so that the breath tester inputs the calibrating gas sample, instead of the patient's breath samples.

Figure 14:
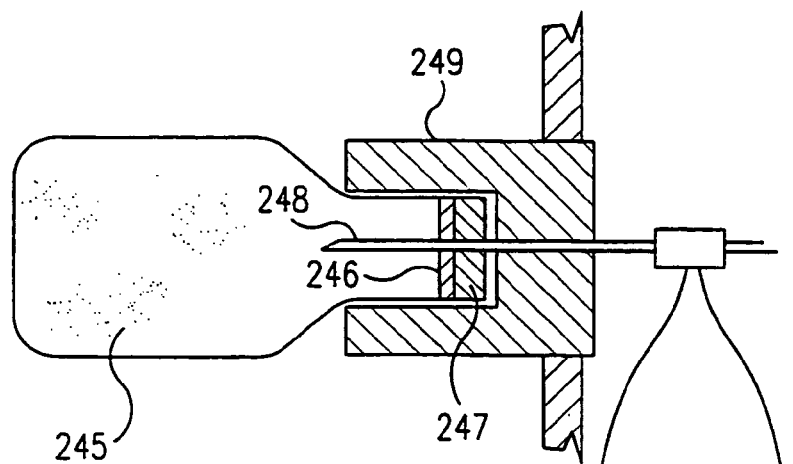
FIG. 14 schematically illustrates another preferred embodiment for the calibration checking gas unit, in which the gas is contained in a metallic housing with a narrow neck for insertion into the calibration input connector on the breath tester front panel.

Reference is now made to FIG. 14 which schematically illustrates another preferred embodiment for the calibration checking gas unit, in which the gas is contained in a metallic housing 245, with a narrow neck for insertion into the calibration checking input connector 249 on the breath tester front panel, in a similar manner to the glass ampoule embodiment shown in FIG. 13. This neck is closed by means of a thin metallic foil 246, preferably of copper or aluminum, hermetically sealed to the metallic housing. The foil is backed with a rubber plate 247. A hollow needle 248 is fixed rigidly in the center of the calibration checking input connector 249, and protrudes therefrom in such a way that, when the calibration checking gas unit is inserted into the connector housing, the needle pierces the rubber plate and the thin metallic foil, so allowing the calibration checking gas to flow through the needle into the breath tester. The narrow bore of the needle acts as a flow restrictor to the calibration checking gas as it flows into the inflatable bag and from there into the porous tube flow system. The gas in the metallic housing is preferably pressurized at 5 bar. The rubber backing plate 247 is operative to provide a hermetic seal between the punctured metallic foil and the needle, so that small movements of the gas calibration checking unit when connected, will not cause leakage of the calibration checking gas during the calibration checking procedure.

The embodiment shown in FIG. 14, being made completely of metal, is able to contain the calibration checking gas without leakage for long periods, providing the calibration checking unit with a long shelf life, typically two years or more. It has an advantage over the glass ampoule embodiment of FIG. 13, in that no glass fragments are produced on use, these being inconvenient, liable to cause injury or damage, or improper connection of the next calibration checking unit if not properly removed.

Figure 15:
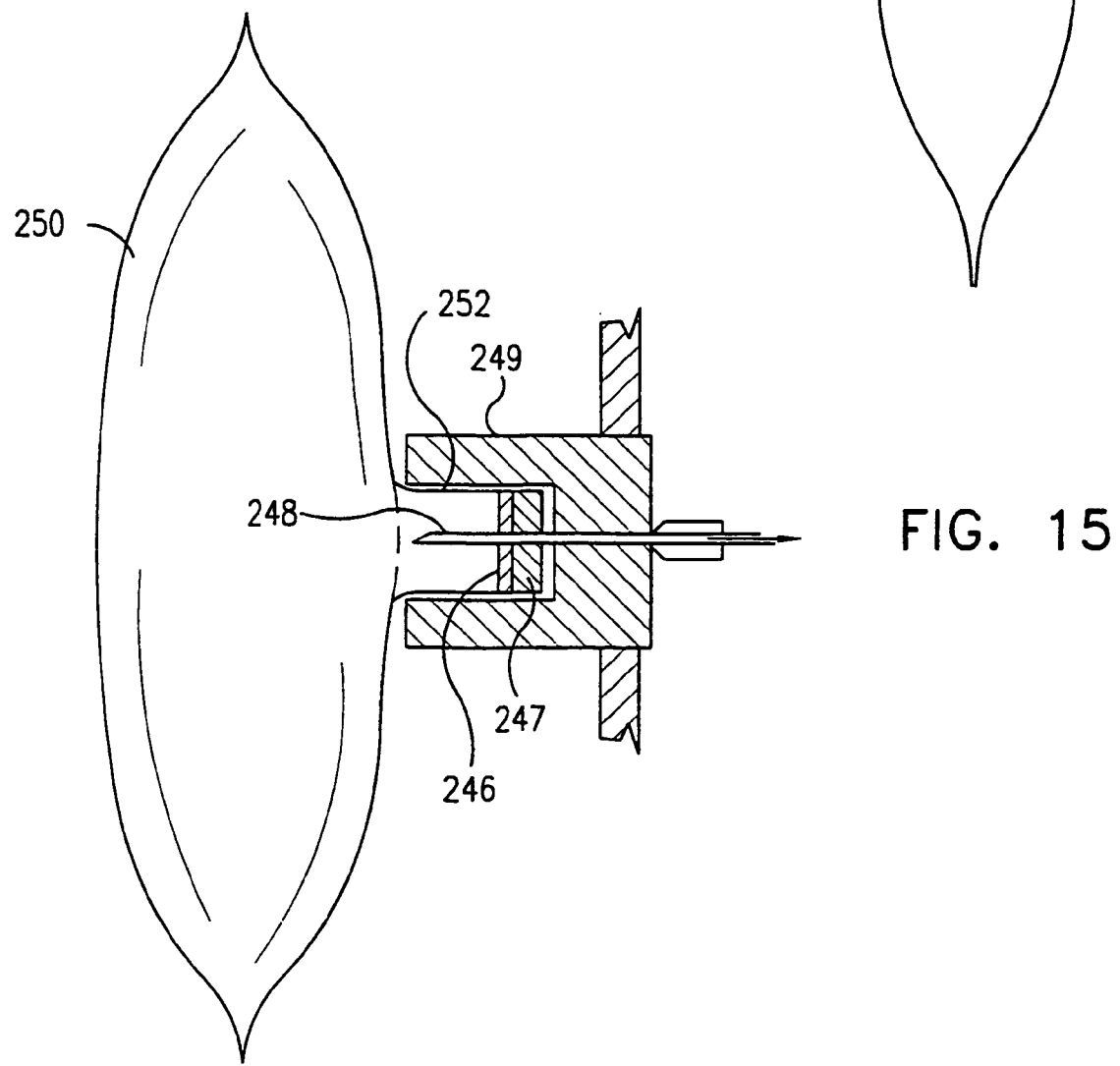
FIG. 15 schematically illustrates another preferred embodiment for the calibration checking gas holder, similar to that shown in FIG. 12, but wherein the gas is contained in a metalized plastic bag.

Reference is now made to FIG. 15 which schematically illustrates yet another preferred embodiment for the calibration checking gas holder, in which the gas is contained in a metalized plastic bag 250. The neck of the bag 252 is similar to that shown in the metallic housing embodiment of FIG. 14, and the bag is connected by means of a similar needle-equipped calibration checking gas input connector 249.

Figure 16A:
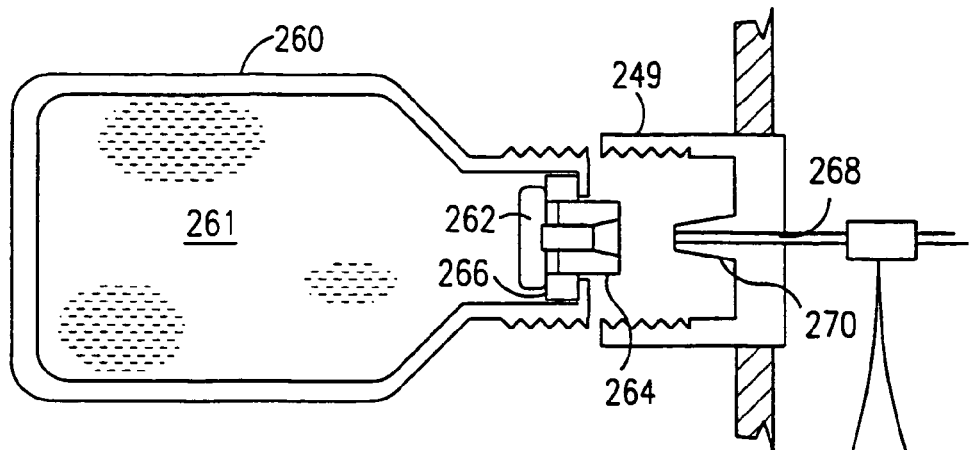
FIG. 16A to FIG. 16C schematically illustrate other preferred embodiments for the calibration gas holder, in which use is made of an aerosol type of container for supplying the calibration gas, with a check valve for containing it.

Reference is now made to FIG. 16A which schematically illustrates another preferred embodiment for the calibration checking gas holder, in which use is made of an aerosol type of container 260 for supplying the calibration checking gas 261. In use, the container screws into a threaded calibration checking input connector 249, from whose center preferably protrudes a conical projection 270, with a narrow gas passage 268 opening into the center of the cone, for conveying the calibration checking gas into the instrument. The gas is held hermetically in the container by means of an aerosol valve assembly, consisting of a valve stem 264, a valve seat 266, and a valve head 262. The valve seat 266 must provide a leak-free seal with the valve head 262, either by use of a layer of properly compliant material, or by the use of an O-ring seal.

Figure 16B:
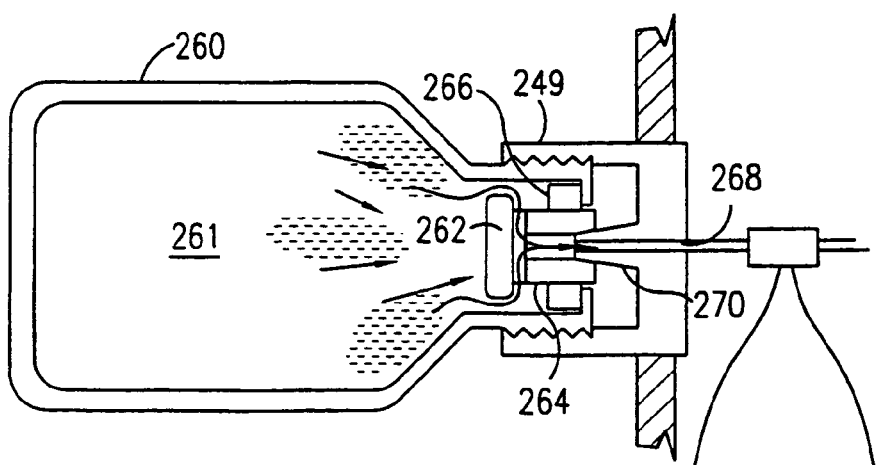

FIG. 16B shows how, as the container is screwed home into the input connector 249, the cone 270 mates with a matching cone in the plunger head 264, and pushes the check valve assembly inwards, thereby allowing the calibration checking check gas to flow through the check valve from the container into the gas passage 268. The matching cones ensure that none of the gas is lost.

Figure 16C:
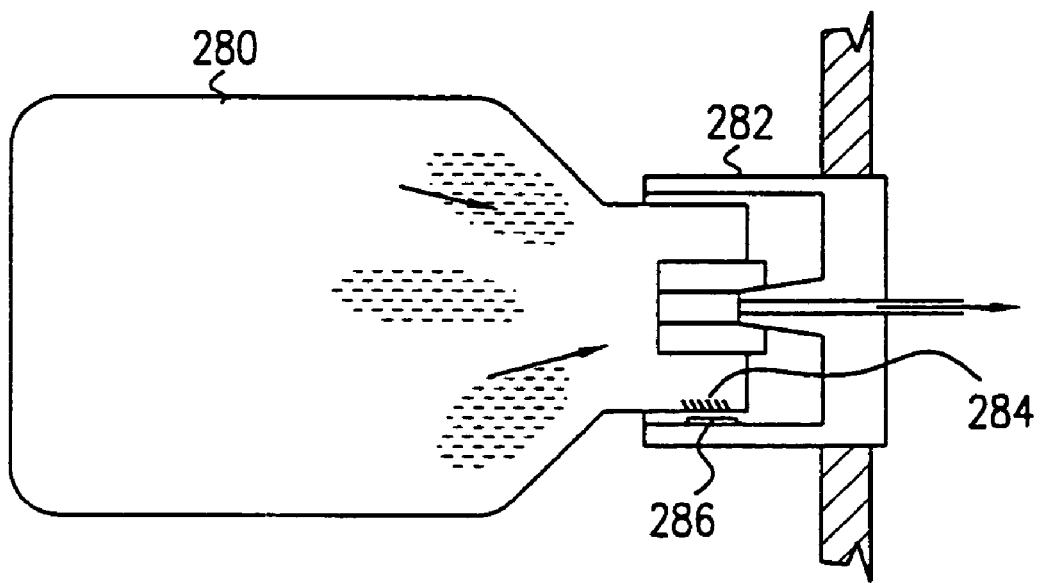

Reference is now made to FIG. 16C, which shows a schematic drawing of a further preferred embodiment for the interfacing of the calibration checking gas container with the input connector, known as the Filterline Recognition System, or FRS. This system includes an electro-optical recognition unit, operative to detect correct placement of the gas container before allowing the calibration checking gas to be released. Confirmation of the correct position also eliminates the possibility of leaks of the calibration checking gas. In addition, the system can also preferably check the identity of the calibration checking gas, and other data such as the serial number of the container or the filling date, to determine its shelf age.

In FIG. 16C is shown a container 280 of calibration checking gas, which is inserted into position in the input connector 282 by means of a pushing action, instead of the screwing action illustrated in FIGS. 16A and 16B. The insertion is preferably performed either manually, or by means of a manually operated mechanism. On the neck of the container is located a reflective label 284, which can be a simple optical reflector, or can contain coded information about the contents, type or age of the gas container. A photoelectric module 286 is mounted in the neck of the input connector. This module consists of a photodiode emitter and a photodetector mounted in close proximity to each other, such modules being well known in the art. The valve in the neck of the container is preferably of the same type as that shown in FIGS. 16A and 16B.

When the gas container is located correctly in position to allow proper and leak-free flow of calibration checking gas into the input connector, optical radiation from the photo-emitter is reflected back from the label 284 into the photodetector part of the module, thereby providing an enabling signal for the calibration checking procedure to commence. According to further preferred embodiments, the photoelectric module can be of a type able to read the information on the label for inputting to the breath tester control system.

This FRS system is an additional embodiment of the invention disclosed and claimed in U.S. patent application Ser. No. 08/961,013, entitled "Fluid Analyzer with Tube Verifier", by some of the inventors of the present application.

Figure 17A:
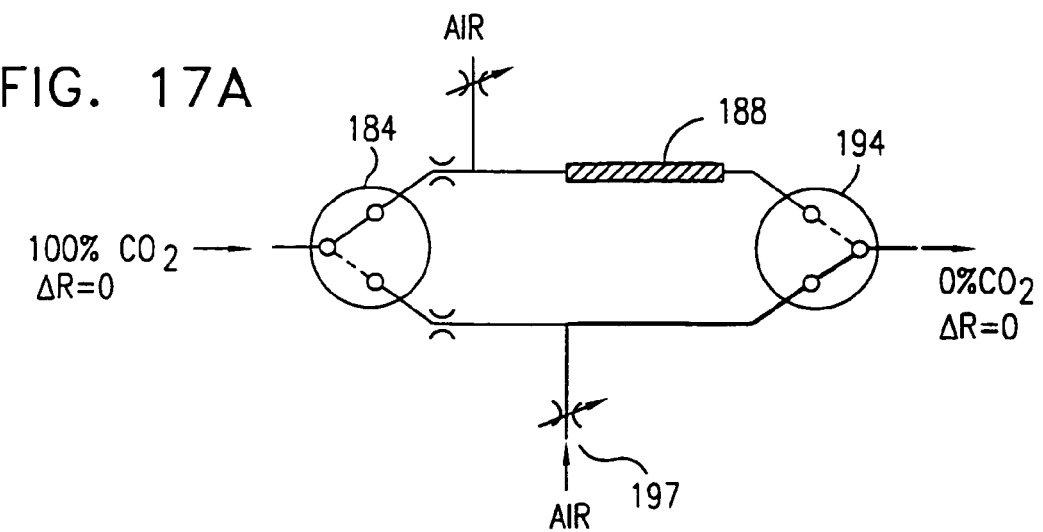
FIGS. 17A to 17C schematically show the operational stages by which a calibration checking procedure is performed in the calibration checking system shown in FIG. 13.
Figure 17B:
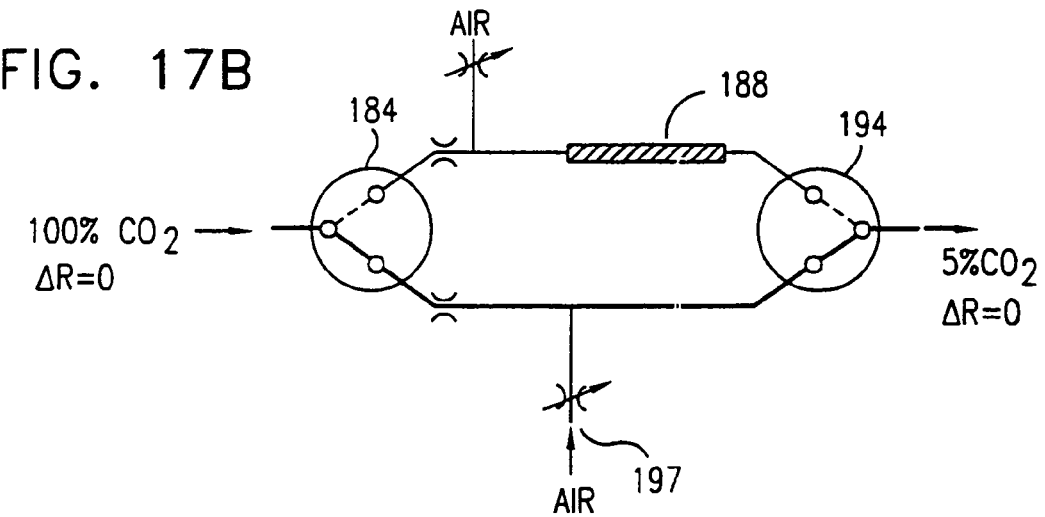
Figure 17C:
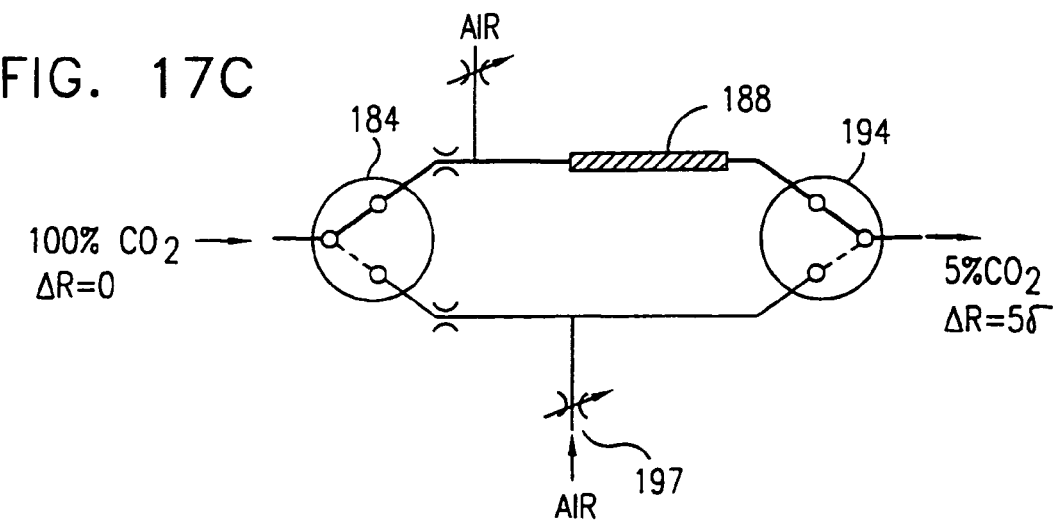

Reference is now made to FIGS. 17A to 17C, which schematically show the operational stages by which a calibration checking procedure is performed in the calibration check system shown in FIG. 13. The requirements of the gas samples generated by the calibration device are that they simulate real patient breaths. Three different types of such samples of gas are required for a complete calibration procedure, as designated below. For each of the types of gas, a 150 ml sample is required by the gas analyzer.

(a) 0% carbon dioxide, representing the inhalation stage of the patient's breath. The generation of this sample is illustrated schematically in FIG. 17A.

(b) 5% carbon dioxide with no isotopic ratio deviation (0δ), representing the exhalation stage of a patient's breath before ingestion of the labeled substrate (or of a patient showing a negative result). The generation of this sample is illustrated schematically in FIG. 17B.

(c) 5% carbon dioxide with 5δ isotopic ratio deviation, representing the exhalation stage of a patient's breath showing a raised level. The generation of this sample is illustrated schematically in FIG. 17C.

In FIG. 17A, solenoid valves 184 and 194 are switched such that only gas from the air inlet 197 in the by-pass path is used in generating the calibration sample. The sample thus has the characteristics: 0% $CO_2$, AR=0.

In FIG. 17B, solenoid valves 184 and 194 are switched such that undiluted carbon dioxide from the by-pass path is used in generating the calibration sample. The sample thus has the characteristics: 5% $CO_2$, AR=0.

In FIG. 17C, solenoid valves 184 and 194 are switched such that only diluted carbon dioxide with an amended isotopic ratio which comes from the path containing the porous tube 188, is used in generating the calibration sample. The sample thus has the characteristics: 5% $CO_2$, AR=5δ.

The rate of switching of the solenoid 184 simulates the "respiration rate" of the calibration pseudo-breath samples.

The total reservoir requirement for the calibration gas can be calculated from the three calibration gas samples mentioned above.

Sample (a) contains no carbon dioxide calibration gas at all.

Sample (b) uses 150 ml. of gas, of which 5% is carbon dioxide. Requirement is thus 7.5 ml.

Sample (c) uses 150 ml. of gas, of which 20% is carbon dioxide (since the input gas to the porous tube contains 20% $CO_2$). Requirement is thus 30 ml.

Total minimum carbon dioxide requirement is thus 37.5 ml at STP, which dictates the use of a container with 40 ml volume at STP to provide some reserve.

The calibration procedure and unit described in the above preferred embodiments thus provides a check of the system calibration at a level of change in the $^{13}CO_2/^{12}CO_2$ ratio very close to the threshold level above which a breath test is considered to give a definite positive result from the patient's breath samples. For this reason, quite apart from its use as a periodic calibration check of the breath tester, it can also be used as a speedy sensitivity check of the instrument at any time, for determining whether a specific patient's results which are on the borderline of being considered positive, are being correctly measured by the instrument.

Figure 18:
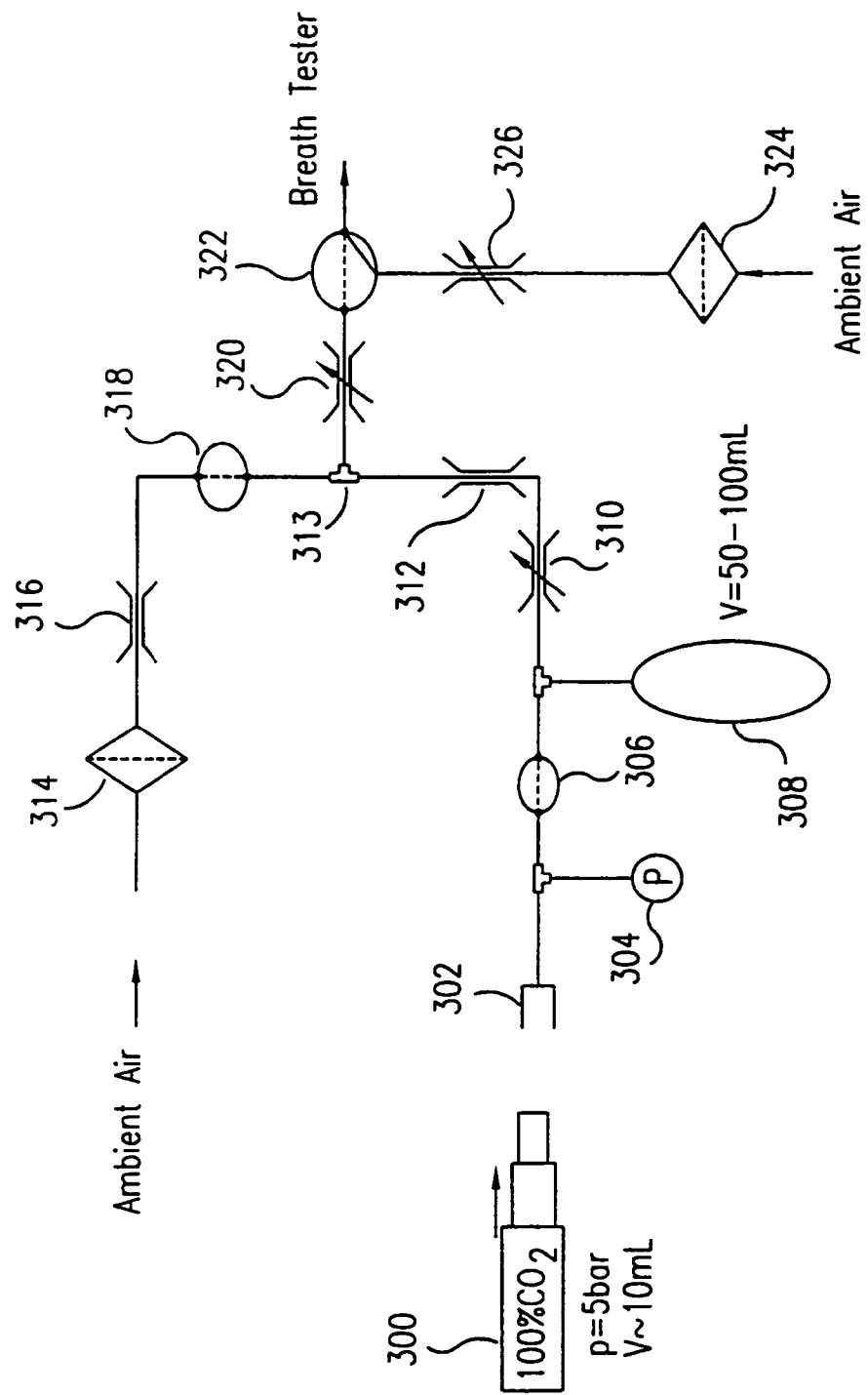
FIG. 18 shows an alternative preferred embodiment for performing a calibration checking procedure, differing from that shown in FIG. 13 in that gas with only one known isotopic ratio is provided to the instrument for measurement.

Reference is now made to FIG. 18, which shows an alternative preferred embodiment to that shown in FIG. 13, for performing a calibration checking procedure. This embodiment differs in that gas with only one known isotopic ratio is provided to the instrument for measurement. This gas is preferably supplied in a container 300 at an elevated pressure, typically 5 bar, so that the volume of the container is suitably compact. The container 300 is preferably of the aerosol-type, as shown in FIG. 16A, and on insertion into the calibrating gas connector 302 on the breath tester front panel, the calibration gas flows through the check valve into the system, and encounters a solenoid valve 306. This valve is generally shut, to isolate the breath tester from the ambient air, but when the pressure monitor 304 senses the presence of the high pressure gas, it provides a signal for the instrument control to open the solenoid valve 306, allowing the gas charge to enter the system, and to inflate the bladder 308, thus providing a reservoir of 100% calibrating gas, $CO_2$ in the embodiment shown, with a known isotopic ratio δ, and at atmospheric pressure, ready for pneumatic handling by the calibrating system. The solenoid 306 is also useful for providing a long-term air tight seal at the system entry, since the connector 302 is intended for short term use only.

The gas flows via a variable flow restrictor 310, which is used for fine tuning the flow through a fixed flow restrictor 312, to a Tee junction 313, where it is diluted down to a useable 5% concentration by mixing with ambient air, ingested into the system via a dust filter 314, a flow restrictor 316, and a solenoid valve 318 opened when a calibration check is to be performed. The values of the flow restrictors 310, 312, 316 are chosen to ensure the proper dilution ratios to achieve the preferred 5% concentration. From the Tee-junction 313, when the 3-way solenoid valve 322 is appropriately set, the gas flows into the breath tester for measurement of its isotopic ratio. Another flow restrictor 320 ensures the correct flow rate into the gas analyzer. The inhalation stage of the subject's breath is simulated by switching solenoid valve 322 to allow ingest of ambient air into the breath tester, via a dust filter 324 and a flow restrictor 326. By switching the solenoid valve 322, the inhaled and exhaled breaths of the subject can be simulated.

The pressure monitor 304 preferentially fulfills more control functions than that of signaling when a container has been connected. First of all, it can verify that the container connected is indeed a new container, and with the correct full pressure of calibrating gas in it. Additionally, it can provide the calibration control system with the information that a new calibration check container has been installed, and that the breath test counter should be reset to zero, ready for counting the permitted number of tests before a new calibration check is mandated by the system.

As already mentioned, the calibration check processes and the devices described hereinabove are part of a mandatory system check incorporating a calibration check, which should be performed at regular intervals during the use of the breath tester instrument. This is a routine operator calibration check, which is mandated by the need to positively verify the accuracy of the breath tester to avoid the occurrence of false positive or false negative results in patients. The calibration check control system of the breath tester must therefore include a procedure which determines when a new calibration check needs to be performed, and supervises that the test is indeed executed using a new calibration check gas kit.

Figure 19A:
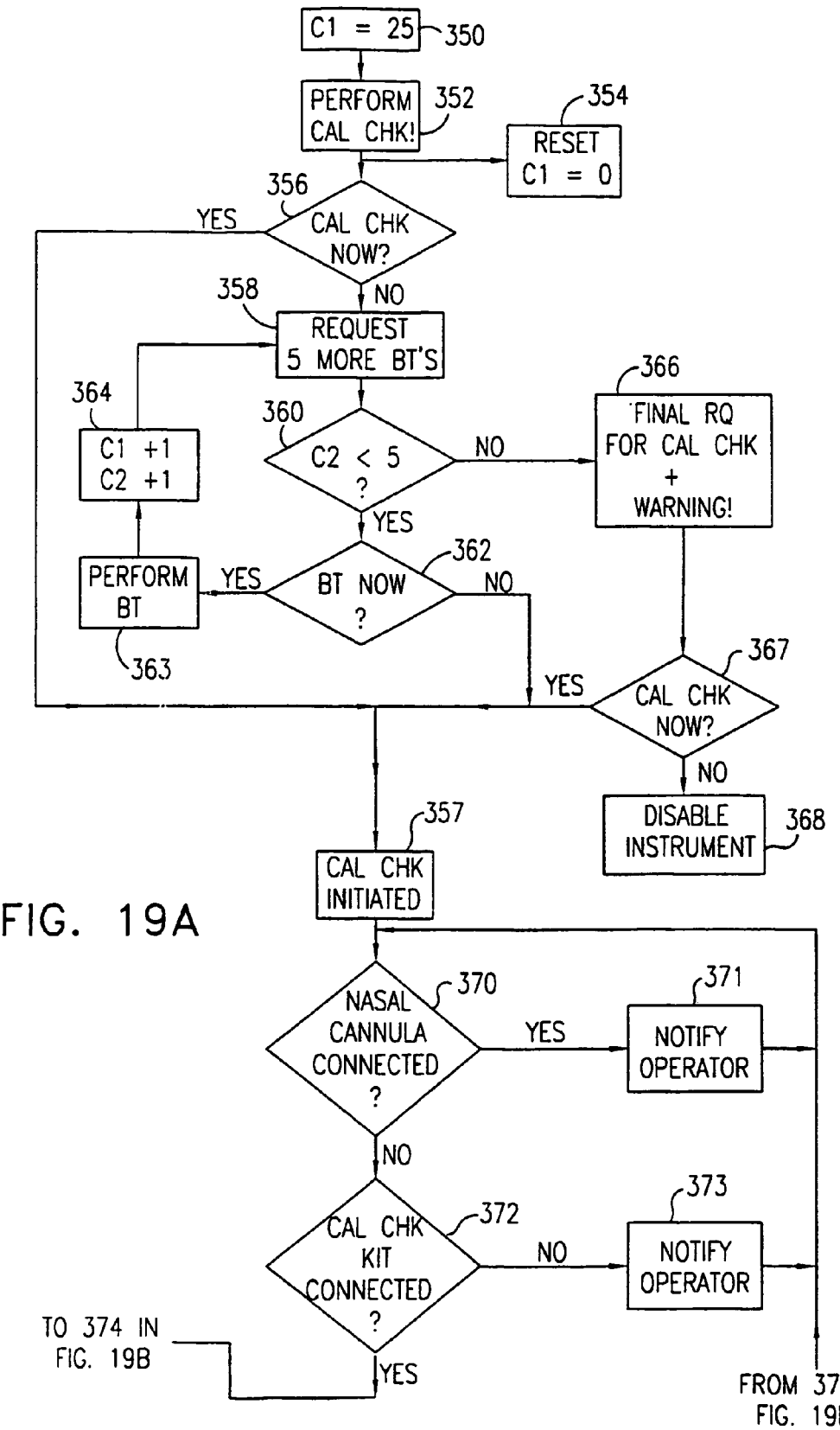
FIGS. 19A–B shows a flow chart, according to a further preferred embodiment of the present invention, of the computational method running within the calibration checking control program, to supervise the demand and execution of the periodic calibration checking tests.
Figure 19B:
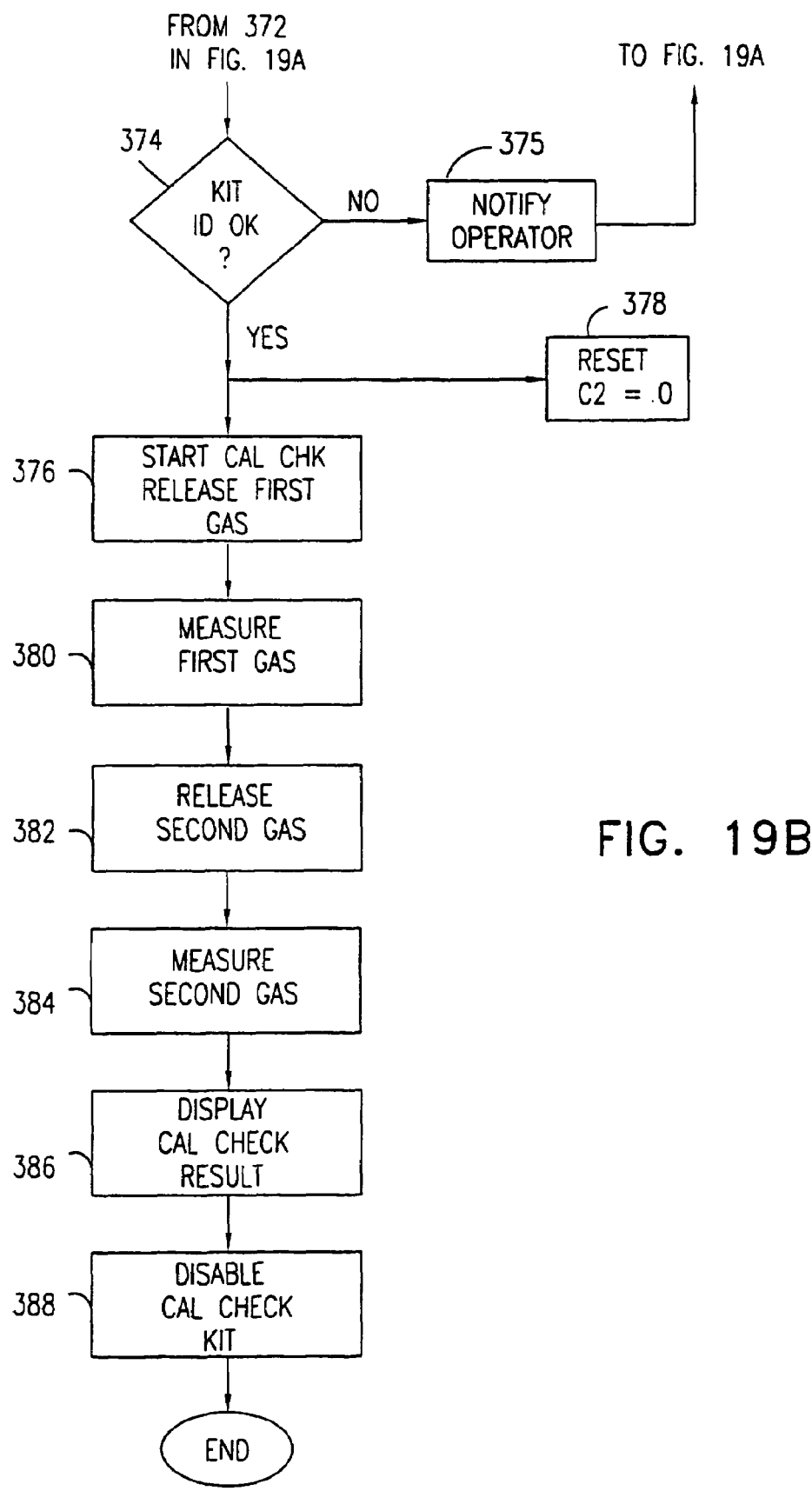

Reference is now made to FIGS. 19A–B, which shows a flow chart, according to a further preferred embodiment of the present invention, of the computational method running within the calibration check control program, to supervise the demand and execution of the periodic calibration checks. A new calibration check is mandated preferably after every 25 breath tests. The main system requirements include that a warning be given to the operator, of the need for a new calibration checking procedure after the execution of 25 breath tests from the previous calibration check. The 25th test may, however, fall exactly during the course of a series of related breath tests, or at an inopportune time, such as just one or two tests before the completion of the day's work, when the need to perform a calibration check would cause unnecessary delay to personnel or patients. For this reason, the calculation method is designed to allow an optional five further tests beyond the authorized 25, before the instrument is completely disabled pending a new calibration check.

At step 350, the breath test primary counter C1 reaches a value 25 since it was last reset to zero by execution of the previous calibration check.

At step 352, a message is displayed to inform the operator that a calibration check is due, and that a new calibration check kit should be connected to the breath tester. At the same time, at step 354, C1 is reset to 0.

At step 356, the operator is asked whether to initiate a calibration check now. If the response is affirmative, the calibration check is initiated at step 357.

A negative response indicates that the operator requests, at step 358, the execution of up to a further 5 tests before a calibration check becomes mandatory.

In such a case, at step 360, the procedure initiates a check that there are still some tests remaining of the allowed extra 5. This is done by monitoring that the secondary counter C2 reads less than 5.

If the secondary counter has reached a value of 5, then a final request for a calibration check is issued to the user at step 366, together with a warning that no more tests will be permitted until the calibration check is performed.

At step 367, the operator is asked whether to initiate a calibration check. If the response is negative, then the calculation method disables the instrument at step 368. If the response is in the affirmative, then the calibration check is initiated at step 357.

If the secondary counter, read at step 360, is not yet at 5, the operator is asked at step 362 whether he wishes to perform an additional breath test before the calibration check. If the response is negative, then the calibration check is initiated at step 357.

If the response is in the affirmative, then at step 363, the first of the extra tests requested is enabled. After performing the test, at step 364, both the primary and secondary counters, C1 and C2 are advanced by 1, and at step 358, the calculation procedure is operative to enable the operator to carry on performing more of the five additional tests requested by him.

Once the calibration check is initiated at step 357, the system first checks, at step 370, whether a nasal cannula is connected, which may prevent the ingestion of pure air for the porous tube device of the calibration check kit.

If the response is positive, then at step 371, the operator is notified thereof and requested to remove the cannula, and control is returned to step 370 to check whether the cannula has indeed been removed.

If the response is negative, then at step 372, a check is made as to whether a calibration check kit is attached or not. If the response is negative, then at step 373, the operator is notified thereof and requested to connect a calibration check kit, and control is returned to step 370 to check for the absence of a nasal cannula again, and at step 372, for the presence of a calibration check kit.

If the response is positive, then at step 374, the identity data of the new calibration check kit is interrogated, to ensure that it is the correct kit for the tests being performed, and that it is indeed a new kit.

If the response is negative, then at step 372, the operator is notified of the problem, and is returned to step 370 to recommence the routine for performing calibration check.

If the response at step 374 is positive, then at step 376, the calibration checking procedure is commenced by the release of the first calibration gas.

Release of the first gas signals the actual commencement of the calibration checking procedure, and the secondary counter C2 is thus reset to zero at step 378.

From this point onwards, the calibration check is described in terms of a two-gas system. At step 380, the first gas is measured, following which, the second gas is released at step 382, and measured at step 384.

At step 386, the result of the calibration check is displayed, and recommended action provided to the operator regarding the need to initiate an operator calibration procedure, as described hereinabove.

At step 388, the identity data of the new calibration check kit is amended by one of the preferred methods described hereinabove to indicate that the kit has been used, and is therefore invalid for further use. The calibration checking procedure is thereby terminated.

For a single gas calibration check, using the intermediate chamber system of the breath tester to dilute that one sample down to provide more calibration points if desired, a similar calculation method is used, with slightly amended steps 380 to 384.

It will be appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A calibration checking device for use with a gas analyzer, comprising:
    a calibration checking unit; and
    a calibration checking unit releasing a calibration checking gas of known composition into said gas analyzer; and
    an enabling mechanism actuated by use of said calibration checking unit and enabling operation of said gas analyzer.

2. A calibration checking device for use with a gas analyzer according to claim 1 and wherein said enabling mechanism is operative to count the number of tests performed by said gas analyzer.

3. A calibration checking device for use with a gas analyzer according to claim 1 and wherein said enabling mechanism is operative to accumulate the time of operation of said gas analyzer.

4. A calibration checking device for use with a gas analyzer according to claim 1 and also comprising a filter for removing fluids from a gas to be analyzed.

5. A calibration checking device for use with a gas analyzer according to claim 4 and wherein said enabling mechanism for enabling operation of said gas analyzer is operated by said filter.

6. A calibration checking device for use with a gas analyzer according to claim 4 and wherein said filter is a section of a sampling tube having built-in fluid filtering properties.

7. A calibration checking device for use with a gas analyzer according to claim 1 and wherein said enabling mechanism is communicative with said gas analyzer by means of a signal selected from a group consisting of electrical, electronic, optical, mechanical, magnetic, pneumatic and gaseous signals.

8. A calibration checking device for use with a gas analyzer according to claim 1 and wherein said enabling mechanism is operative to ensure proper location of said calibration checking unit.

9. A calibration checking device for use with a gas analyzer according to claim 1 and wherein said enabling mechanism comprises an optical transmitter and a receiver, the optical path between which is completed by reflection from said calibration checking unit only when said calibration checking unit is properly located in said gas analyzer.

10. A calibration checking device for use with a gas analyzer according to claim 1 and wherein said enabling mechanism is actuated by release of said calibration checking gas.

11. A calibration checking device for use with a gas analyzer according to claim 1 and wherein said enabling mechanism is actuated by means of an active integrated circuit disposed on said calibration checking device.

12. A calibration checking device for use with a gas analyzer according to claim 11 and also comprising a filter for removing fluids from a gas to be analyzed.

13. A calibration checking device for use with a gas analyzer according to claim 12 and wherein said filter comprises a drying agent disposed in proximity to at least part of an inside wall of said sampling tube.

14. A calibration checking device for use with a gas analyzer according to claim 1 and wherein said enabling mechanism is operative to accumulate the time since the last calibration check of said gas analyzer.

15. A calibration checking device for use with a gas analyzer, comprising:

a calibration checking unit releasing a calibration checking gas of known composition into said gas analyzer; and a count actuating mechanism initiated by first use of said calibration checking device, operative to begin a count of the number of tests performed with said calibration checking device.

16. A calibration checking device for use with a gas analyzer according to claim 15 and also comprising a filter for removing fluids from the gas to be analyzed.

17. A calibration checking device for use with a gas analyzer according to claim 16 and wherein said count actuating mechanism is actuated by said filter.

18. A calibration checking device for use with a gas analyzer according to claim 15 and wherein said count actuating mechanism is actuated by said calibration checking unit.

19. A calibration checking device for use with a gas analyzer according to claim 15 and wherein said count is used to prevent use of said gas analyzer after a predetermined number of tests have been performed.

20. A calibration checking device for use with a gas analyzer according to claim 15 and wherein said count of the number of tests performed with said calibration checking device is performed within the gas analyzer.

21. A calibration checking device for use with a gas analyzer according to claim 15 and wherein said count of the number of tests performed with said calibration checking device is performed within the calibration checking device.

22. A calibration checking device for use with a gas analyzer according to claim 15 and wherein said count actuating mechanism is communicative with said gas analyzer by means of a signal selected from a group including electrical, electronic, optical, mechanical, magnetic, pneumatic and gaseous signals.

23. A calibration checking device for use with a gas analyzer according to claim 15 and wherein said calibration checking unit releases a calibration checking gas of known composition into said gas analyzer.

24. A calibration checking device for use with a gas analyzer according to claim 23 and wherein said count actuating mechanism is actuated by release of said calibration gas.

25. A calibration checking device for use with a gas analyzer according to claim 15 and wherein said count actuating mechanism is actuated by means of an active integrated circuit disposed on said calibration checking device.

26. A calibration checking device for use with a gas analyzer according to claim 15, and also comprising a disenabling device which prevents said count actuating mechanism from being reinitiated after first use of said calibration checking device.

* * * * *